US012379368B2

(12) United States Patent
Stappenbeck et al.

(10) Patent No.: US 12,379,368 B2
(45) Date of Patent: Aug. 5, 2025

(54) METHODS FOR DETERMINING THERAPEUTIC RESPONSIVENESS FOR INFLAMMATORY BOWEL DISEASE THERAPY

(71) Applicant: Washington University, St. Louis, MO (US)

(72) Inventors: Thaddeus Stappenbeck, St. Louis, MO (US); Kelli VanDussen, St. Louis, MO (US)

(73) Assignee: Washington University, St. Louis, MO (US)

( * ) Notice: Subject to any disclaimer, the term of this patent is extended or adjusted under 35 U.S.C. 154(b) by 718 days.

(21) Appl. No.: 17/473,747

(22) Filed: Sep. 13, 2021

(65) Prior Publication Data

US 2022/0082548 A1    Mar. 17, 2022

Related U.S. Application Data

(60) Provisional application No. 63/077,346, filed on Sep. 11, 2020.

(51) Int. Cl.
*G01N 33/483*    (2006.01)

(52) U.S. Cl.
CPC ..... *G01N 33/4833* (2013.01); *G01N 2800/52* (2013.01)

(58) Field of Classification Search
None
See application file for complete search history.

(56) References Cited

U.S. PATENT DOCUMENTS

2006/0105419 A1* 5/2006 Blankenberg ........ G01N 33/573
                                                               435/25
2010/0303813 A1* 12/2010 Carulli ...................... A61P 1/04
                                                               435/7.8

OTHER PUBLICATIONS

Van Der Vekiens et al., Human and equine cardiovascular endocrinology: beware to compare, Cardiovascular Endocrinology 2013, vol. 2, No. 4, pp. 67-76. (Year: 2013).*
Torzewski et al., Animal Models of C-Reactive Protein, Hindawl Publishing Corporation, Mediators of Inflammation, vol. 2014, Article ID 683598, 2014, pp. 1-7. (Year: 2014).*
Goswami et al., Ultra structural changes in tight junctions and other cellular elements in treatment naive celiac diseaseand active Crohn's disease, IndianJ Gastroenterol, Nov. 2011, 30 (SUppl 1): A31-32. (Year: 2011).*
Schurmann et al., Transepithelial transport processes at the intestinal mucosa in inflammatory bowel disease, Int J Colorect Dis, 1999, 14, pp. 41-46. (Year: 1999).*
Arijs et al., Mucosal gene signatures to predict response to infliximab in patients with ulcerative colitis. Gut. Dec. 2009;58(12):1612-9.

Atreya et al., In vivo imaging using fluorescent antibodies to tumor necrosis factor predicts therapeutic response in Crohn's disease. Nat Med. Mar. 2014;20(3):313-8.
Feagan et al., Ustekinumab as Induction and Maintenance Therapy for Crohn's Disease. N Engl J Med. Nov. 17, 2016;375(20):1946-1960.
Feagan et al., Vedolizumab as induction and maintenance therapy for ulcerative colitis. N Engl J Med. Aug. 22, 2013;369(8):699-710.
Haberman et al., Pediatric Crohn disease patients exhibit specific ileal transcriptome and microbiome signature. J Clin Invest. Aug. 2014;124(8):3617-33.
Kawamoto et al., Anti-integrin therapy for multiple sclerosis. Autoimmune Dis. 2012;2012:357101. 1-6.
Liu et al., Epithelial cell extrusion leads to breaches in the intestinal epithelium. Inflamm Bowel Dis. Apr. 2013;19(5):912-21.
Murthy et al., Introduction of anti-TNF therapy has not yielded expected declines in hospitalisation and intestinal resection rates in inflammatory bowel diseases: a population-based interrupted time series study. Gut. Feb. 2020;69(2):274-282.
Niederreiter et al., ER stress transcription factor Xbp1 suppresses intestinal tumorigenesis and directs intestinal stem cells. J Exp Med. Sep. 23, 2013;210(10):2041-56.
Osterman et al., Mucosal Biomarker of Innate Immune Activation Predicts Response to Vedolizumab in Crohn's Disease. Inflamm Bowel Dis. Sep. 18, 2020;26(10):1554-1561.
Park et al., The Cost of Inflammatory Bowel Disease: An Initiative From the Crohn's & Colitis Foundation. Inflamm Bowel Dis. Jan. 1, 2020;26(1):1-10.
Peery et al., Burden and Cost of Gastrointestinal, Liver, and Pancreatic Diseases in the United States: Update 2018. Gastroenterology. Jan. 2019;156(1):254-272.e11.
Present et al., Infliximab for the treatment of fistulas in patients with Crohn's disease. N Engl J Med. May 6, 1999;340(18):1398-405.
Rutgeerts et al., Infliximab for induction and maintenance therapy for ulcerative colitis. N Engl J Med. Dec. 8, 2005;353(23):2462-76.
Sandborn et al., Ustekinumab induction and maintenance therapy in refractory Crohn's disease. N Engl J Med. Oct. 18, 2012;367(16):1519-28.
Sandborn et al., Vedolizumab as induction and maintenance therapy for Crohn's disease. N Engl J Med. Aug. 22, 2013;369(8):711-21.
Sandler et al., The burden of selected digestive diseases in the United States. Gastroenterology. May 2002;122(5):1500-11.
Schirmer et al., Dynamics of metatranscription in the inflammatory bowel disease gut microbiome. Nat Microbiol. Mar. 2018;3(3):337-346.

(Continued)

*Primary Examiner* — Gary Counts
(74) *Attorney, Agent, or Firm* — Jason R. Bond; Casimir Jones, S.C.

(57) ABSTRACT

The present disclosure provides methods of selecting a treatment for an inflammatory bowel disease in a subject. In particular, using an indicator of epithelial absorption and metabolism the present disclosure provides method for determining the likelihood a subject is responsive or non-responsive to an inflammatory bowel disease therapeutic agent. The method includes providing a baseline measurement of a microvillus length in the small intestine of a subject, selecting a treatment for the subject according to a treatment criteria, and administering the treatment to the subject.

4 Claims, 6 Drawing Sheets

(56) References Cited

OTHER PUBLICATIONS

Shen-Orr et al., Computational deconvolution: extracting cell type-specific information from heterogeneous samples. Curr Opin Immunol. Oct. 2013;25(5):571-8.

Stappenbeck et al., Extranuclear sequestration of phospho-Jun N-terminal kinase and distorted villi produced by activated Rac1 in the intestinal epithelium of chimeric mice. Development. Jul. 2001;128(13):2603-14.

Targan et al., A short-term study of chimeric monoclonal antibody cA2 to tumor necrosis factor alpha for Crohn's disease. Crohn's Disease cA2 Study Group. N Engl J Med. Oct. 9, 1997;337(15):1029-35.

Tew et al., Association Between Response to Etrolizumab and Expression of Integrin αE and Granzyme A in Colon Biopsies of Patients With Ulcerative Colitis. Gastroenterology. Feb. 2016;150(2):477-87.e9.

Toedter et al., Gene expression profiling and response signatures associated with differential responses to infliximab treatment in ulcerative colitis. Am J Gastroenterol. Jul. 2011;106(7):1272-80.

VanDussen et al., Abnormal Small Intestinal Epithelial Microvilli in Patients With Crohn's Disease. Gastroenterology. Sep. 2018;155(3):815-828.

Vermeire et al., Etrolizumab as induction therapy for ulcerative colitis: a randomised, controlled, phase 2 trial. Lancet. Jul. 26, 2014;384(9940):309-18.

Verstockt et al., Low TREM1 expression in whole blood predicts anti-TNF response in inflammatory bowel disease. EBioMedicine. Feb. 2019;40:733-742.

West et al., Oncostatin M drives intestinal inflammation and predicts response to tumor necrosis factor-neutralizing therapy in patients with inflammatory bowel disease. Nat Med. May 2017;23(5):579-589.

* cited by examiner

METHODS FOR DETERMINING THERAPEUTIC RESPONSIVENESS FOR INFLAMMATORY BOWEL DISEASE THERAPY

CROSS REFERENCE TO RELATED APPLICATION

This application claims the benefit of U.S. Provisional Application No. 63/077,346, filed Sep. 11, 2020 the disclosure of which is herein incorporated by reference in its entirety.

FIELD OF THE TECHNOLOGY

The present invention relates to the fields of biology and medicine. It would be useful to identify inflammatory bowel disease patients who will benefit from treatment.

BACKGROUND

Inflammatory bowel disease (IBD) describes a group of disorders in which the intestines become inflamed. Specific examples of IBD include ulcerative colitis and Crohn's disease (CD). Ulcerative colitis is limited to the colon or large intestine. Crohn's disease, on the other hand, can involve any part of the gastrointestinal tract from the mouth to the anus. Most commonly, though, it affects the last part of the small intestine or the colon or both. The exact etiology of ulcerative colitis and Crohn's is unknown, but certain factors have been found to be associated with the disease, including genetic factors, immune system reactions, environmental factors, nonsteroidal anti-inflammatory drug (NSAID) use, low levels of antioxidants, psychological stress factors, a smoking history, microbial infection and consumption of milk products.

The treatment of IBD typically uses a stepwise approach to the use of medications in which the least harmful drugs or drugs are taken for a short period of time while the patient's responsiveness is monitored. If this initial treatment fails to provide relief, more potent medications from a higher step are used. This process continues until the patient achieves relief. To date, no objective criteria have been developed for selecting a therapy for IBD.

It is therefore of great interest to develop new approaches for predicting responsiveness to treatment for IBD.

SUMMARY OF THE DISCLOSURE

The present disclosure is based on the unexpected discovery of a mucosal marker of malabsorption, e.g. microvillus length (MVL) as disclosed herein, to be useful in determining a subject's responsiveness to anti-inflammatory bowel disease treatment, such as anti-IL-12/23 treatment, anti-α4β7 integrin treatment, anti-TNFα treatment, and/or steroid treatment.

Accordingly, in one aspect the present disclosure provides methods for assessing responsiveness to an inflammatory bowel disease (IBD) therapy in a subject having IBD by (a) measuring microvillus length in a biological sample obtained from the subject; and (b) assessing the subject's responsiveness to an IBD therapy based on at least the microvillus length. In some embodiments, the subject has Crohn's disease or ulcerative colitis In some embodiments, the inflammatory bowel disease therapy is selected from an anti-IL12/23 therapy (e.g. ustekinumab), an anti-integrin therapy (e.g. vedolizumab), an anti-TNF therapy and a steroid therapy. In some embodiments, the biological sample is a tissue biopsy where the tissue biopsy is from the small intestine. In some embodiments, the tissue biopsy is from the ileum. In some embodiments, measuring microvillus length includes determining the microvillus length of one or more enterocytes.

In some embodiments, the method further comprises comparing the measured microvillus length to a pre-determined value. In one aspect, the pre-determined value is the microvillus length in a control subject or control population that is responsive to the inflammatory bowel disease therapy and the subject is determined to be responsive or likely to be responsive to the inflammatory bowel disease therapy when the microvillus length is the same or above the pre-determined value or the subject is determined to be non-responsive or likely to be non-responsive to the inflammatory bowel disease therapy when the microvillus length is the below the pre-determined value.

In another aspect, the pre-determined value is the microvillus length in a control subject or control population that is non-responsive to the inflammatory bowel disease therapy and the subject is determined to be responsive or likely to be responsive to the inflammatory bowel disease therapy when the microvillus length is the above the pre-determined value or the subject is determined to be non-responsive or likely to be non-responsive to the inflammatory bowel disease therapy when the microvillus length is the same or below the pre-determined value.

In another aspect, the subject is determined to be responsive or likely to be responsive to an inflammatory bowel disease therapy when the microvillus length is at least about 1.7 μm or above or the subject is determined to be non-responsive or likely to be non-responsive to an inflammatory bowel disease therapy when the microvillus length is about 1.69 μm or below. In still another aspect, the subject is determined to be responsive or likely to be responsive to an inflammatory bowel disease therapy when the microvillus length is at least between about 1.35 μm and about 1.55 μm.

In some embodiments, the assessment of the subject's responsiveness to the IBD therapy is further based on one or more clinical factors such as gene expression values, ileal intestinal epithelial cell (IEC) pyroptosis, disease severity, or the presence or absence of one or more bacterial populations.

In each of the preceding embodiments, the methods may further comprising subjecting the subject to a suitable treatment of IBD based on the assessment of the subject's responsiveness to the IBD therapy where when the subject is determined to be responsive to the IBD therapy and the method further comprises administering a pharmaceutical composition to the subject, for treating IBD.

In another aspect the present disclosure provides methods for selecting an inflammatory bowel disease (IBD) therapy for a subject having IBD by (a) measuring microvillus length in a biological sample obtained from the subject; and (b) assessing the subject's responsiveness to the IBD therapy based on at least the microvillus length. In some embodiments, the subject has Crohn's disease or ulcerative colitis In some embodiments, the inflammatory bowel disease therapy is selected from an anti-IL12/23 therapy (e.g. ustekinumab), an anti-integrin therapy (e.g. vedolizumab), an anti-TNF therapy and a steroid therapy. In some embodiments, the biological sample is a tissue biopsy where the tissue biopsy is from the small intestine. In some embodiments, the tissue biopsy is from the ileum. In some embodiments, measuring microvillus length includes determining the microvillus length of one or more enterocytes.

In some embodiments, the method further comprises comparing the measured microvillus length to a pre-determined value. In one aspect, the pre-determined value is the microvillus length in a control subject or control population that is responsive to the inflammatory bowel disease therapy and the subject is determined to be responsive or likely to be responsive to the inflammatory bowel disease therapy when the microvillus length is the same or above the pre-determined value or the subject is determined to be non-responsive or likely to be non-responsive to the inflammatory bowel disease therapy when the microvillus length is the below the pre-determined value.

In another aspect, the pre-determined value is the microvillus length in a control subject or control population that is non-responsive to the inflammatory bowel disease therapy and the subject is determined to be responsive or likely to be responsive to the inflammatory bowel disease therapy when the microvillus length is the above the pre-determined value or the subject is determined to be non-responsive or likely to be non-responsive to the inflammatory bowel disease therapy when the microvillus length is the same or below the pre-determined value.

In another aspect, the subject is determined to be responsive or likely to be responsive to an inflammatory bowel disease therapy when the microvillus length is at least about 1.7 μm or above or the subject is determined to be non-responsive or likely to be non-responsive to an inflammatory bowel disease therapy when the microvillus length is about 1.69 μm or below. In still another aspect, the subject is determined to be responsive or likely to be responsive to an inflammatory bowel disease therapy when the microvillus length is at least between about 1.35 μm and about 1.55 μm.

In some embodiments, the assessment of the subject's responsiveness to the IBD therapy is further based on one or more clinical factors such as gene expression values, ileal intestinal epithelial cell (IEC) pyroptosis, disease severity, or the presence or absence of one or more bacterial populations.

In some embodiments, when the subject is determined to be non-responsiveness or likely to be non-responsive to the IBD therapy based on the corresponding microvillus length, a different type of therapy is selected for the subject or when the subject is determined to be responsive or likely to be response to the IBD therapy the IBD therapy is selected and optionally the method further comprises administering a pharmaceutical composition comprising the IBD therapy to the subject, for treating IBD.

In still another aspect, the present disclosure provides methods for treating an inflammatory bowel disease (IBD) in a subject in need thereof by (a) measuring microvillus length in a biological sample obtained from the subject; (b) assessing the subject's responsiveness to the IBD therapy based on at least the microvillus length; and (c) administering a pharmaceutical composition to the subject for treating IBD. In some embodiments, the subject has Crohn's disease or ulcerative colitis In some embodiments, the inflammatory bowel disease therapy is selected from an anti-IL12/23 therapy (e.g. ustekinumab), an anti-integrin therapy (e.g. vedolizumab), an anti-TNF therapy and a steroid therapy. In some embodiments, the biological sample is a tissue biopsy where the tissue biopsy is from the small intestine. In some embodiments, the tissue biopsy is from the ileum. In some embodiments, measuring microvillus length includes determining the microvillus length of one or more enterocytes.

In some embodiments, the method further comprises comparing the measured microvillus length to a pre-determined value. In one aspect, the pre-determined value is the microvillus length in a control subject or control population that is responsive to the inflammatory bowel disease therapy and the subject is determined to be responsive or likely to be responsive to the inflammatory bowel disease therapy when the microvillus length is the same or above the pre-determined value or the subject is determined to be non-responsive or likely to be non-responsive to the inflammatory bowel disease therapy when the microvillus length is the below the pre-determined value.

In another aspect, the pre-determined value is the microvillus length in a control subject or control population that is non-responsive to the inflammatory bowel disease therapy and the subject is determined to be responsive or likely to be responsive to the inflammatory bowel disease therapy when the microvillus length is the above the pre-determined value or the subject is determined to be non-responsive or likely to be non-responsive to the inflammatory bowel disease therapy when the microvillus length is the same or below the pre-determined value.

In another aspect, the subject is determined to be responsive or likely to be responsive to an inflammatory bowel disease therapy when the microvillus length is at least about 1.7 μm or above or the subject is determined to be non-responsive or likely to be non-responsive to an inflammatory bowel disease therapy when the microvillus length is about 1.69 μm or below. In still another aspect, the subject is determined to be responsive or likely to be responsive to an inflammatory bowel disease therapy when the microvillus length is at least between about 1.35 μm and about 1.55 μm.

In some embodiments, the assessment of the subject's responsiveness to the IBD therapy is further based on one or more clinical factors such as gene expression values, ileal intestinal epithelial cell (IEC) pyroptosis, disease severity, or the presence or absence of one or more bacterial populations.

In some embodiments, when the subject is determined to be non-responsiveness or likely to be non-responsive to the IBD therapy based on the corresponding microvillus length, a different type of therapy is selected for the subject or when the subject is determined to be responsive or likely to be response to the IBD therapy the IBD therapy is selected and optionally the method further comprises administering a pharmaceutical composition comprising the IBD therapy to the subject, for treating IBD.

In still another embodiment, the present disclosure provides methods for selecting a subject into a clinical trial for an inflammatory bowel disease therapy by (a) measuring microvillus length in a biological sample obtained from the subject; (b) assessing the subject's responsiveness to the IBD therapy based on at least the microvillus length; (c) selecting the subject into a clinical trial when the subject is determined to be responsive or likely to be responsive based on the measured microvillus length. In some embodiments, the subject has Crohn's disease or ulcerative colitis. In some embodiments, the biological sample is a tissue biopsy where the tissue biopsy is from the small intestine. In some embodiments, the tissue biopsy is from the ileum. In some embodiments, measuring microvillus length includes determining the microvillus length of one or more enterocytes.

In some embodiments, the method further comprises comparing the measured microvillus length to a pre-determined value. In one aspect, the pre-determined value is the microvillus length in a control subject or control population that is responsive to the inflammatory bowel disease therapy and the subject is determined to be responsive or likely to be responsive to the inflammatory bowel disease therapy when the microvillus length is the same or above the pre-determined value or the subject is determined to be non-responsive or likely to be non-responsive to the inflammatory bowel disease therapy when the microvillus length is the below the pre-determined value.

In another aspect, the pre-determined value is the microvillus length in a control subject or control population that is non-responsive to the inflammatory bowel disease therapy and the subject is determined to be responsive or likely to be responsive to the inflammatory bowel disease therapy when the microvillus length is the above the pre-determined value or the subject is determined to be non-responsive or likely to be non-responsive to the inflammatory bowel disease therapy when the microvillus length is the same or below the pre-determined value.

In another aspect, the subject is determined to be responsive or likely to be responsive to an inflammatory bowel disease therapy when the microvillus length is at least about 1.7 μm or above or the subject is determined to be non-responsive or likely to be non-responsive to an inflammatory bowel disease therapy when the microvillus length is about 1.69 μm or below. In still another aspect, the subject is determined to be responsive or likely to be responsive to an inflammatory bowel disease therapy when the microvillus length is at least between about 1.35 μm and about 1.55 μm.

In some embodiments, the assessment of the subject's responsiveness to the IBD therapy is further based on one or more clinical factors such as gene expression values, ileal intestinal epithelial cell (IEC) pyroptosis, disease severity, or the presence or absence of one or more bacterial populations.

The details of one or more embodiments of the invention are set forth in the description below. Other features or advantages of the present invention will be apparent from the following drawings and detailed description of several examples, and also from the appended claims.

BRIEF DESCRIPTION OF THE FIGURES

FIG. 1A graphically depicts the probability of responsiveness to ustekinumab relative to microvillus length. Ileal microvillus length is an effect modifier of clinical response to ustekinumab (N=95). FIG. 1B shows a bar graph showing the greatest therapeutic effect and differences were seen in the normal microvillus group. Clinical response to ustekinumab stratified by pre-treatment microvillus length (N=95). FIG. 1C is a bar graph showing clinical remission rates. Clinical remission to ustekinumab stratified by pre-treatment ileal microvillus length (N=95). FIG. 1D graphically depicts the therapeutic effect by endoscopic response. Endoscopic response to ustekinumab stratified by pre-treatment ileal microvillus length (N=71).

FIG. 2A graphically depicts the microvillus length was not correlated with baseline clinical disease activity, as measured by CDAI. Clinical disease activity by CDAI (N=95). FIG. 2B shows microvillus length was not correlated with baseline endoscopic disease activity by SES-CD. Endoscopic disease activity by SES-CD (N=95).

FIG. 3A shows the probability curve of clinical response to microvillus length. Clinical response as a function of ileal microvillus length (N=64). FIG. 3B shows graphically that pretreatment microvillus length did not correlate with baseline clinical disease activity by HBI. Correlation between ileal microvillus length and baseline clinical disease activity by the Harvey-Bradshaw Index (HBI) (N=64). FIG. 3C shows graphically that pretreatment microvillus length did not correlate with baseline endoscopic disease activity by SES-CD. Correlation between ileal MV length and baseline endoscopic disease activity by SES-CD (N=58).

FIG. 4A graphically depicts pre-treatment microvillus length does not correlate with pre-treatment ileal IEC pyroptosis. Correlation between ileal MICROVILLUS LENGTH and ileal IEC pyroptosis on pre-treatment biopsy samples (N=64). FIG. 4B shows ileal IEC pyroptosis and ileal microvillus length is associated with clinical response rate. Improved discriminant ability for responders from non-responders to vedolizumab (N=64).

DETAILED DESCRIPTION

Figure 1A:
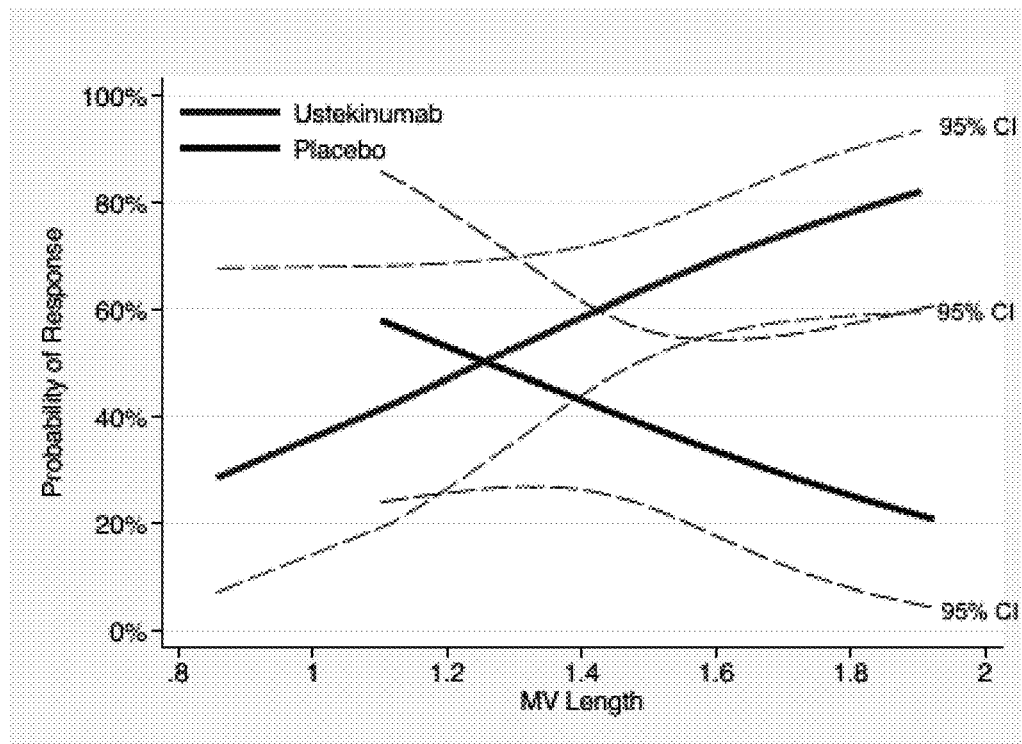
FIG. 1A, FIG. 1B, FIG. 1C, and FIG. 1D show ileal microvillus length is predictive of therapeutic response to ustekinumab in CD patients from the UNITI-2 randomized controlled clinical trial.

The present disclosure is based, at least in part, form the discovery that assessment of the epithelial cellular function of a subject is predictive for determining whether that subject suffering from or disposed to suffer from a bowel disorder such as chronic inflammatory bowel disease or irritable bowel syndrome will be responsive to a therapeutic agent. In particular, Applicants have discovered that certain methods to quantify microvillus length in the small intestine can be used to determine responsive or non-responsiveness to a therapeutic agent. Thus, a subject identified according to the disclosure may benefit from treatment with an agent that treats inflammatory bowel disease (or less commonly irritable bowel syndrome), such as an agent that blocks α4β7 integrin (e.g., vedolizumab) or an agent that targets interleukin-12/23 (e.g., Ustekinumab) or an agent that blocks tumor necrosis factor, among others inflammatory bowel disease treatments.

Therapeutic efficacy of biologics has remained at about 50% for 2 decades. To improve the understanding of inflammatory bowel disease processes and its potential clinical personalized translation, the predictive value of an epithelial cell biomarker, ileal microvillus length (MVL), was examined in Crohn's disease (CD) patients. A standardized approach was applied using ileal biopsies from a UNITI-2 randomized controlled trial were analyzed in a 5-center academic retrospective cohort of CD patients. The correlation between ileal microvillus length and therapeutic success was determined.

Based on the microvillus length analysis disclosed herein, epithelial cellular function correlating to IBD subjects' responsiveness/non-responsiveness to certain IBD treatment have been identified and reported herein. Such epithelial cellular function can be relied on to determine suitable treatment or adjust current IBD therapy for subjects who need the treatment. Other aspects and iterations of the invention are described more thoroughly below.

I. Assessing Therapeutic Responsiveness/Non-Responsiveness

One aspect of the present disclosure relates to methods for assessing responsiveness or non-responsiveness of a IBD subject (e.g., a human having ulcerative colitis or Crohn's disease) would be responsive or non-responsive to a therapeutic agent (e.g., steroid therapy such as a corticosteroid therapy, anti-IL-12/23, anti-TNF therapy, and/or anti-α4β7 integrin therapy) based on the microvillus length of the small intestine, as disclosed herein. As used herein, assessing "responsiveness" or "non-responsiveness" to a therapeutic agent refers to the determination of the likelihood of a subject for responding or not responding to the therapeutic agent.

(a) Determination of Microvillus Length

Microvillus, as used herein, refers to microscopic cellular membrane protrusions that increase the surface area for diffusion and minimize any increase in volume, and are involved in a wide variety of functions, including absorption, secretion, cellular adhesion, and mechanotransduction. Microvillus are covered in plasma membrane, which encloses cytoplasm and microfilaments. Though these are cellular extensions, there are little or no cellular organelles present in the microvillus.

Each microvillus has a dense bundle of cross-linked actin filaments, which serves as its structural core. 20 to 30 tightly bundled actin filaments are cross-linked by bundling proteins fimbrin (or plastin-1), villin and espin to form the core of the microvillus.

In the enterocyte microvillus, the structural core is attached to the plasma membrane along its length by lateral arms made of myosin 1a and $Ca^{2+}$ binding protein calmodulin. Myosin 1a functions through a binding site for filamentous actin on one end and a lipid binding domain on the other. The plus ends of the actin filaments are located at the tip of the microvillus and are capped, possibly by capZ proteins, while the minus ends are anchored in the terminal web composed of a complicated set of proteins including spectrin and myosin II.

Thousands of microvillus form a structure called the brush border that is found on the apical surface of some epithelial cells, such as the small intestines. Microvillus should not be confused with intestinal villi, which are made of many cells. Each of these cells has many microvillus.

To determine microvillus length, for use in the methods disclosed herein, in a biological sample of a candidate subject can be measured by using assays disclosed herein, e.g., those described below and in Example 1.

A subject to be assessed by any of the methods described herein can be a mammal, e.g., a human. A subject having may be diagnosed based on clinically available tests and/or an assessment of the pattern of symptoms in a subject and response to therapy. In some embodiments, the subject is a subject having or suspected of having Crohn's disease. In some embodiments, the subject is a subject having or suspected of having ulcerative colitis.

As used herein, the term "biological sample" refers to a sample obtained from a subject. A suitable biological sample can be obtained from a subject as described herein via routine practice. Non-limiting examples of biological samples include fluid samples such as blood (e.g., whole blood, plasma, or serum), urine, and saliva, and solid samples such as tissue (e.g., skin, lung, or nasal) and feces. Such samples may be collected using any method known in the art or described herein. In some embodiments the biological sample can be an intestinal, colon and/or rectal biopsy sample. In one specific example, the biological sample ileum biopsy.

As will be appreciated by a skilled artisan, the method of collecting a biological sample can and will vary depending upon the nature of the biological sample and the type of analysis to be performed. Any of a variety of methods generally known in the art may be utilized to collect a biological sample. Generally speaking, the method preferably maintains the integrity of the cells and tissue such that the microvillus length can be accurately detected and measured according to the disclosure.

In some embodiments, a single sample is obtained from a subject to detect microvillus length in the sample. Alternatively, microvillus length may be detected in samples obtained over time from a subject. As such, more than one sample may be collected from a subject over time. For instance, 2, 3, 4, 5, 6, 7, 8, 9, 10, 11, 12, 13, 14, 15, 16 or more samples may be collected from a subject over time. In some embodiments, 2, 3, 4, 5, or 6 samples are collected from a subject over time. In other embodiments, 6, 7, 8, 9, or 10 samples are collected from a subject over time. In yet other embodiments, 10, 11, 12, or more hours are collected from a subject over time. In other embodiments, 14, 15, 16 or more samples are collected from a subject over time.

When more than one sample is collected from a subject over time, samples may be collected every 0.5, 1, 2, 3, 4, 5, 6, 7, 8, 9, 10, 11, 12 or more hours. In some embodiments, samples are collected every 0.5, 1, 2, 3, or 4 hours. In other embodiments, samples are collected every 4, 5, 6, or 7 hours. In yet other embodiments, samples are collected every 7, 8, 9, or 10 hours. In other embodiments, samples are collected every 10, 11, 12 or more hours. Additionally, samples may be collected every 1, 2, 3, 4, 5, 6, 7, 8, 9, 10, 11, 12 or more days. In some embodiments, a sample is collected about every 6 days. In some embodiments, samples are collected every 1, 2, 3, 4, or 5 days. In other embodiments, samples are collected every 5, 6, 7, 8, or 9 days. In yet other embodiments, samples are collected every 9, 10, 11, 12 or more days.

Once obtained from the subject, the biological sample can then be processed for imaging. Methodology to quantitatively assess microvillus length include transmission electron microscopy (TEM), scanning electron microscopy (SEM), fluorescent microscopy, bright field (e.g., Hematoxylin and Eosin staining). Generally speaking, measurement of microvillus length is perpendicular to the membrane. In general, these techniques involve fixing the cells or tissue, cutting thin sections of the cell or tissue, and staining the cells or tissues.

In some embodiments, determining microvillus length of a subject includes measuring the microvillus length of at least 1 enterocyte, at least 2 enterocytes, at least 3, at least 4 enterocytes, at least 5 enterocytes, at least 6 enterocytes, at least 7 enterocytes, at least 8 enterocytes, at least 9 enterocytes, or at least 10 enterocytes or more per villus. Thus, in some embodiments, microvillus length of a subject includes measuring at least 10 cells per sample, at least 20 cells per sample, at least 30 cells per sample, at least 40 cells per sample, at least 50 cells per sample, or at least 60 or more cells per sample. In preferred embodiments, the measured cells are located in the top one-third of a villus, where enterocytes have a matured brush border, or in regions with well-oriented epithelial cells.

In some embodiments, determining microvillus length of a subject includes measuring the microvillus length of one or more enterocytes on at least 1 villi, at least 2 villi, at least 3 villi, at least 4 villi, at least 5 villi, at least 6 villi, at least 7 villi, at least 8 villi, at least 9 villi or at least at least 1 villi or more per sample.

Selection of measurements and choice of mathematical operations for determining microvillus length may be optimized to maximize specificity of the method. In still further embodiments, measured levels of microvillus length may be used in various mathematical operations to improve the predictive power compared to each by itself. In an exemplary embodiment, a protocol for measuring microvillus length outlined in the Examples is used. Based on the microvillus length disclosed herein, a therapeutic responsiveness can be obtained via, e.g., a computational program. Various computational programs can be applied in the methods of this disclosure to aid in analysis of the microvillus length data for producing outcome data.

(b) Assessing Therapeutic Responsiveness Based on Microvillus Length and Optionally Other Factors The microvillus length of a candidate subject as disclosed herein can be used for assessing whether the subject's responsiveness or non-responsiveness to an inflammatory bowel disease therapy, for example, an anti-IL-12/23 therapy, an anti-α4β7 integrin therapy, an anti-TNFα therapy, or a steroid therapy. For example, the microvillus length of a candidate subject can be compared with a pre-determined value to determine the subject's responsiveness or non-responsiveness.

A pre-determined value may represent the microvillus length of a control subject or represent the microvillus length of a control population. In some examples, the microvillus length of a control subject or a control population may be determined by the same method as used for determining the microvillus length the candidate subject. In some instances, the control subject or control population may refer to a healthy subject or healthy subject population of the same species (e.g., a human subject or human subject population having no IBD). Alternatively, the control subject or control population may be an IBD subject or IBD subject population who is responsive to any of the therapeutic agents disclosed herein. In other instances, the control subject or control population may be an IBD subject or IBD subject population who is non-responsive to the therapeutic agent.

It is to be understood that the methods provided herein do not require that a pre-determined value be measured every time a candidate subject is tested. Rather, in some embodiments, it is contemplated that the pre-determined value can be obtained and recorded and that any test level can be compared to such a pre-determined level. The pre-determined level may be a single-cutoff value or a range of values.

By comparing the microvillus length of a candidate subject as disclosed herein and a pre-determined value as also described herein, the subject can be identified as responsive or likely to be responsive or as not responsive or not likely to be responsive to an IBD treatment based on the assessing.

For example, when the pre-determined value represents the microvillus length of IBD subjects who are responsive to a therapy, derivation from such a pre-determined value would indicate non-responsiveness to the therapy. Alternatively, when the pre-determined value represents the microvillus length of IBD subjects who are non-responsive to a therapy, derivation from such a pre-determined value would indicate responsiveness to the therapy. In some instances, derivation means that the microvillus length (e.g., represented by a score) of a candidate subject is elevated or reduced as relative to a pre-determined value, for example, by at least 5%, 10%, 20%, 30%, 40%, 50%, 60%, 70%, 80%, 90%, 100%, 150%, 200%, 300%, 400%, 500% or more above or below the pre-determined value.

In some embodiments, a subject is determined to be responsive to a IBD therapeutic when the microvillus length of the subject is about 1.7 μm or greater. Thus, in some embodiments, a subject is determined to be non-responsive to an IBD therapeutic when the microvillus length of the subject is about 1.6 μm or below. In another aspect, a subject is determined to be responsive to a IBD therapeutic when the microvillus length of the subject is between about 1.3 μm and about 1.6 μm.

In addition to the microvillus length, a subject's responsive or non-responsiveness to the treatment disclosed herein may further take into consideration one or more clinical factors. Exemplary clinical factors include, but are not limited to, mucosal and blood biomarkers (e.g., oncostatin M, TNFR2, IL13RA2, and TREM1), and ileal intestinal epithelial cell (IEC) pyroptosis. Methods for detecting a measuring RNA and protein expression levels are known in the art and contemplated herein. Methods for measuring ileal intestinal epithelial cell (IEC) pyroptosis include protocols discussed in the below example.

Alternatively or in addition, assessing responsiveness or non-responsiveness of a subject may further comprise factors such as microbial populations in the biological sample, such as rectal biopsy of the subject. In that case, any of the methods disclosed herein may further comprise analyzing microbial populations in the biological sample. Microbial populations can be determined using methods well known in the art, including, for example, 16S RNA gene sequencing. Ribosomal RNA genes from a biological samples, microcolonies or cultures from a subject having UC can be amplified by PCR by using specific 16S RNA oligonucleotide primers for bacteria. After cloning the PCR products, the inserts are screened by their restriction patterns (RFLP—restriction fragment length polymorphism). The clones can be submitted to sequence analysis and compared with known 16S RNA genes using, for example, the online GenBank database. In this way, it can be determined which microorganism species are present or absent.

In one example, a method of the present disclosure comprises (a) providing a biological sample obtained from a subject and measuring microvillus length in the sample; (b) comparing the microvillus length to a pre-determined value; and (c) determining the subject as responsive to an inflammatory bowel disease therapy when the microvillus length is the same or above the pre-determined value, where the predetermined value is the microvillus length in a control population responsive to the inflammatory bowel disease therapy.

In another example, a method of the present disclosure comprises (a) providing a biological sample obtained from a subject and measuring microvillus length in the sample; (b) comparing the microvillus length to a pre-determined value; and (c) determining the subject as non-responsive to an inflammatory bowel disease therapy when the microvillus length is below the pre-determined value, where the predetermined value is the microvillus length in a control population responsive to the inflammatory bowel disease therapy.

In still another example, a method of the present disclosure comprises (a) providing a biological sample obtained from a subject and measuring microvillus length in the sample; (b) comparing the microvillus length to a pre-determined value; and (c) determining the subject as responsive to an inflammatory bowel disease therapy when the microvillus length is above the pre-determined value, where the predetermined value is the microvillus length in a control population non-responsive to the inflammatory bowel disease therapy.

In still yet another example, a method of the present disclosure comprises (a) providing a biological sample obtained from a subject and measuring microvillus length in the sample; (b) comparing the microvillus length to a pre-determined value; and (c) determining the subject as non-responsive to an inflammatory bowel disease therapy when the microvillus length is the same or below the pre-determined value, where the predetermined value is the microvillus length in a control population non-responsive to the inflammatory bowel disease therapy.

In yet another example, a method of the present disclosure comprises (a) providing a biological sample obtained from a subject and measuring microvillus length in the sample; (b) comparing the microvillus length to a pre-determined value; and (c) determining the subject as non-responsive to an inflammatory bowel disease therapy when the microvillus length is the same or below the pre-determined value, where the predetermined value is the microvillus length in a control population non-responsive to the inflammatory bowel disease therapy.

In another example, a method of the present disclosure comprises (a) providing a biological sample obtained from a subject and measuring microvillus length in the sample; and (b) determining the subject as responsive to an inflammatory bowel disease therapy when the microvillus length is at least about 1.7 µm or above.

In one example, a method of the present disclosure comprises (a) providing a biological sample obtained from a subject and measuring microvillus length in the sample; and (b) determining the subject as non-responsive to an inflammatory bowel disease therapy when the microvillus length is about 1.69 µm or below.

In another example, a method of the present disclosure comprises (a) providing a biological sample obtained from a subject and measuring microvillus length in the sample; and (b) determining the subject as responsive to an inflammatory bowel disease therapy when the microvillus length is at least between about 1.35 µm and about 1.55 µm.

In each of the above embodiments, the methods may comprise selecting an IBD therapeutic agent based on the subject's determined responsiveness or non-responsiveness to the therapeutic agent. In one aspect, the subject may have previously been administered a therapeutic agent for an IBD. In some instances, the subject may be free of a prior treatment for IBD.

II. Methods of Treatment

Another aspect of the present disclosure is a method for treating a subject in need thereof. The terms "treat," "treating," or "treatment" as used herein, refers to the provision of medical care by a trained and licensed professional to a subject in need thereof. The medical care may be a diagnostic test, a therapeutic treatment, and/or a prophylactic or preventative measure. The object of therapeutic and prophylactic treatments is to prevent or slow down (lessen) an undesired physiological change or disease/disorder. Beneficial or desired clinical results of therapeutic or prophylactic treatments include, but are not limited to, alleviation of symptoms, diminishment of extent of disease, stabilized (i.e., not worsening) state of disease, a delay or slowing of disease progression, amelioration or palliation of the disease state, and remission (whether partial or total), whether detectable or undetectable. Symptoms of IBD are well known and include, without limitation, diarrhea, fever (e.g., low-grade fever), abdominal pain and cramping, blood in the stool (hematochezia), bleeding ulcers, bloating, bowel obstruction, unintended weight loss, and anemia. Crohn's disease, ulcerates colitis, indeterminate colitis, and chemotherapy-induced colitis are all forms of inflammatory bowel disease.

In one embodiment, a method for treating a subject as described above may comprise (a) obtaining a biological sample from a subject and measuring, in the sample, microvillus length; and (b) administering a pharmaceutical composition to the subject when the subject is determined to be responsive to the inflammatory bowel disease treatment.

In addition to using a measurement of microvillus length in any of the above embodiments, one or more additional factors (e.g., gene expression and ileal intestinal epithelial cell (IEC) pyroptosis) can be calculated and may be used. Mathematical operations other than an average may also be used. For instance, various statistical models (e.g., linear regressions, LME curves, LOESS curves, etc.) in conjunction with other known biomarkers may be used.

When a subject is determined to be responsive or non-responsive based on any of the microvillus length disclosed herein, this subject could be subjected to a suitable treatment for inflammatory bowel disease, including any of the ulcerative colitis or Chron's disease treatments known in the art and disclosed herein.

As used herein, by the term "anti-TNF therapy" is meant the administration, to a subject (e.g., a human subject), of an agent that inhibits tumor necrosis factor (referred to as TNF or TNF alpha). Several such anti-TNF agents are commercially available and have been approved for use in human subjects. Any anti-TNF agent, where a biological or a small molecule, is contemplated in the disclosure. In some embodiments, anti-TNF agent may be adalimumab, infliximab, certolizumab pegol, golimumab, or etanercept. Yet additional non-limiting anti-TNF agents are those that inhibit production of TNF (e.g., TNF-alpha) by cells by, for example, inhibiting enzymes (e.g., protein kinases) in the cells to inhibit their production of TNF. One such anti-TNF agent that acts to prevent TNF-alpha production is apremilast.

As used herein, by the term "anti-integrin therapy" is meant the administration, to a patient, of an agent that inhibits an integrin from forming an adhesion with its natural target. Thus, an anti-integrin agent, when bound to the integrin, partially or completely prevents the integrin from binding its target. Integrins are family of transmembrane receptors that appear on a variety of cells. They are heterodimers comprised of two chains—an alpha chain and a beta chain. In mammals, there are eighteen alpha chains and eight beta chains, so a particular integrin may be referred to by which alpha chain and which beta chain it has. Some non-limiting examples of integrins are the $\alpha1\beta1$ integrin (also called VLA-1), the $\alpha4\beta7$ integrin (also called LPAM-1), and the $\alpha1\beta2$ integrin (also called LFA-1). An anti-integrin agent is an agent that inhibits (i.e., blocks) any integrin family member (i.e., inhibits one or more integrin family member).

In some embodiments, the anti-integrin agent is vedolizumab which targets LPAM-1. In some embodiments, the anti-integrin agent is natalizumab which targets alpha 4 chain integrin(s). In some embodiments, the anti-integrin agent is etrolizumab which targets the $\beta7$ chain integrin(s) (e.g., integrins $\alpha4\beta7$ and $\alpha E\beta7$). Additional anti-integrin agents are described in Kawamoto et al., Autoimmune Diseases, vol. 2012, Article ID 357101, herein incorporated by reference.

In some embodiments, the IBD therapeutic agent inhibits interleukin-12 and interleukin-23 (IL-12 and IL-23, respectively). IL-12 and IL-23 share a common p40 subunit. IL-12 is made up of the IL-12/23p40 and IL-12p35 subunits, and IL-23 comprises IL-23p19 and IL-23p40. Such an agent includes, without limitation, ustekinumab. An agent that inhibits IL-12 and IL-23 will be referred to herein as an "anti-IL12/23 agent).

In some embodiments, a subject is determined to be likely responsive to an anti-IL12/23 therapy, a steroid therapy, an anti-TNFα therapy, or an anti-integrin therapy, using any of the methods described herein, the subject may then be administered an effective amount of an anti-IL12/23 agent, a steroid, an anti-TNFα agent, and/or an anti-integrin agent, for treating IBD. In another aspect, a subject determined to be likely responsive using the methods described herein, may be administered an effective amount of an anti-IL12/23 agent, a steroid, an anti-TNFα agent, and/or an anti-integrin agent for treating IBD.

In some embodiments, a subject is determined to be unlikely responsive to a steroid therapy, an anti-TNFα therapy, or an anti-integrin therapy, using any of the methods described herein, the subject may then be administered an effective amount of an alternative therapeutic agent for treating IBD, for example, a non-steroid, a non-anti-TNFα agent, and/or non-anti-IL12/23 agent and/or non-anti-integrin agent.

Non-limiting examples of steroids include corticosteroids such as methylprednisolone, prednisone, hydrocortisone, and budesonide.

Medications such as sulfasalazine (Azulfadine), mesalamine (Asacol, Pentasa), azathioprine (Imuran), 6-MP (Purinethol), cyclosporine, and methotrexate, can be administered to the subject in an amount effective to treating IBD. In some embodiments, the IBD treatment comprises an anti-inflammatory agent, an immune suppressant agent, an antibiotic agent, or a combination thereof. Non-limiting examples of anti-inflammatory agents include sulfasalazine, mesalamine, balsalazide, olsalazine, or corticosteroids (e.g., prednisone or budesonide). Non-limiting examples of immune suppressant agents include azathioprine, mercaptopurine, cyclosporine, infliximab, adalimumab, certolizumab pegol, methotrexate, or natalizumab. Non-limiting examples of antibiotics include metronidazole and ciprofloxacin. In some embodiments, IBD treatment comprises an anti-diarrheal (e.g., psyllium powder, methylcellulose or loperamide), a laxative, acetaminophen, iron, vitamin B-12, calcium, or vitamin D. In some embodiments, IBD treatment comprises surgery or fecal bacteriotherapy (also called a fecal microbiota transplantation or stool transplant).

Non-limiting examples of surgery include proctocolectomy, ileostomy, or strictureplasty. In some embodiments, UC treatment comprises a therapeutic agent (e.g., an anti-inflammatory agent, an immune suppressant agent, an antibiotic agent, or a combination thereof) and surgery. It is to be understood that any of the IBD treatments described herein may be used in any combination. According to the method disclosed herein, a subject determined to be non-responsive to a therapeutic agent may be administered a non-anti-IL12/23, a non-steroid, non-anti-TNF, or non-anti-integrin therapy for treating IBD, but instead may be treated with surgery.

In one example, the present disclosure provides a method for treating a subject with inflammatory bowel disease (e.g., Crohn's disease or ulcerative colitis) the method comprising (a) providing a biological sample obtained from a subject and measuring, in the sample, microvillus length; (b) comparing the microvillus length to a pre-determined value; (c) determining the subject as responsive to an inflammatory bowel disease therapy; and (d) administering a pharmaceutical composition to the subject when the microvillus length is the same or above the pre-determined value, where the predetermined value is the microvillus length in a control population responsive to the inflammatory bowel disease therapy. Alternatively, if the subject is predicted as not responsiveness to the therapy based on the corresponding microvillus length, a different type of therapy can be applied to the subject.

In still another example, the present disclosure provides a method for treating a subject with inflammatory bowel disease (e.g., Crohn's disease or ulcerative colitis) the method comprising (a) providing a biological sample obtained from a subject and measuring, in the sample, microvillus length; (b) comparing the microvillus length to a pre-determined value; (c) determining the subject as responsive to an inflammatory bowel disease therapy; and (d) administering a pharmaceutical composition to the subject when the microvillus length is above the pre-determined value, where the predetermined value is the microvillus length in a control population non-responsive to the inflammatory bowel disease therapy. Alternatively, if the subject is predicted as not responsiveness to the therapy based on the corresponding microvillus length, a different type of therapy can be applied to the subject.

In another example, the present disclosure provides a method for treating a subject with inflammatory bowel disease (e.g., Crohn's disease or ulcerative colitis) the method comprising (a) providing a biological sample obtained from a subject and measuring, in the sample microvillus length; (b) determining the subject as responsive to an inflammatory bowel disease therapy; and (c) administering a pharmaceutical composition to the subject when the microvillus length is at least about 1.7 μm or above. Alternatively, if the subject is predicted as not responsiveness to the therapy based on the corresponding microvillus length, a different type of therapy can be applied to the subject.

In another example, the present disclosure provides a method for treating a subject with inflammatory bowel disease (e.g., Crohn's disease or ulcerative colitis) the method comprising (a) providing a biological sample obtained from a subject and measuring, in the sample microvillus length; (b) determining the subject as responsive to an inflammatory bowel disease therapy; and (c) administering a pharmaceutical composition to the subject when the microvillus length is at least between about 1.35 μm and about 1.55 μm. Alternatively, if the subject is predicted as not responsiveness to the therapy based on the corresponding microvillus length, a different type of therapy can be applied to the subject.

In each of the above embodiments, a pharmaceutical composition may comprise one or more therapeutic agents disclosed herein or known in the art. In certain aspects, a therapeutically effective amount of a pharmaceutical composition may be administered to a subject. Administration is performed using standard effective techniques, including peripherally (i.e. not by administration into the central nervous system) or locally to the central nervous system. Peripheral administration includes but is not limited to oral, inhalation, intravenous, intraperitoneal, intra-articular, subcutaneous, pulmonary, transdermal, intramuscular, intranasal, buccal, sublingual, or suppository administration. Local administration, includes but is not limited to via a lumbar, intraventricular or intraparenchymal catheter or using a surgically implanted controlled release formulation. The route of administration may be dictated by the disease or condition to be treated.

Pharmaceutical compositions for effective administration are deliberately designed to be appropriate for the selected mode of administration, and pharmaceutically acceptable excipients such as compatible dispersing agents, buffers, surfactants, preservatives, solubilizing agents, isotonicity agents, stabilizing agents, and the like are used as appropriate. Remington's Pharmaceutical Sciences, Mack Publishing Co., Easton Pa., 16Ed ISBN: 0-912734-04-3, latest edition, incorporated herein by reference in its entirety, provides a compendium of formulation techniques as are generally known to practitioners.

For therapeutic applications, a therapeutically effective amount of a composition of the invention is administered to a subject. A "therapeutically effective amount" is an amount of the therapeutic composition sufficient to produce a measurable response. Actual dosage levels of active ingredients in a therapeutic composition of the invention can be varied so as to administer an amount of the active compound(s) that is effective to achieve the desired therapeutic response for a particular subject. The selected dosage level will depend upon a variety of factors including the activity of the therapeutic composition, formulation, the route of administration, combination with other drugs or treatments, age, the symptoms, and the physical condition and prior medical history of the subject being treated. As used herein, the terms "treat", "treatment" and "treating" refer to the reduction or amelioration of the severity, duration and/or progression of a disease or disorder or one or more symptoms thereof resulting from the administration of one or more therapies.

The term "appropriate treatment regimen" refers to the standard of care needed to treat a specific disease or disorder. Often such regimens require the act of administering to a subject a therapeutic agent(s) capable of producing a curative effect in a disease state. Often such regimens require the act of administering to a subject a therapeutic agent(s) capable of producing reduction of symptoms associated with a disease state. Examples such therapeutic agents include, but are not limited to, NSAIDS, acetaminophen, anti-histamines, beta-agonists, anti-tussives or other medicaments that reduce the symptoms associated with the disease process.

In some embodiments, a minimal dose is administered, and dose is escalated in the absence of dose-limiting toxicity. Determination and adjustment of a therapeutically effective dose, as well as evaluation of when and how to make such adjustments, are known to those of ordinary skill in the art of medicine.

The frequency of dosing may be daily or once, twice, three times or more per week or per month, as needed as to effectively treat the symptoms. The timing of administration of the treatment relative to the disease itself and duration of treatment will be determined by the circumstances surrounding the case. Treatment could begin immediately, such as at the site of the injury as administered by emergency medical personnel. Treatment could begin in a hospital or clinic itself, or at a later time after discharge from the hospital or after being seen in an outpatient clinic. Duration of treatment could range from a single dose administered on a one-time basis to a life-long course of therapeutic treatments.

Typical dosage levels can be determined and optimized using standard clinical techniques and will be dependent on the mode of administration.

Any of the methods described herein can further comprise adjusting the IBD treatment performed to the subject based on the results obtained from the methods disclosed herein (e.g., based on microvillus lengths disclosed herein). Adjusting treatment includes, but are not limited to, changing the dose and/or administration of the anti-IBD agent used in the current treatment, switching the current medication to a different anti-IBD agent, or applying a new IBD therapy to the subject, which can be either in combination with the current therapy or replacing the current therapy.

Methods for measuring microvillus length and determining a subject's responsiveness or non-responsiveness are described in Section I and incorporated into this section by reference.

III. Clinical Trials

Another aspect of the present disclosure is a method for selecting a subject into a clinical trial, in particular a clinical trial for an inflammatory bowel disease therapy, provided all other criteria for the clinical trial have been met. In one embodiment, a method for a method for selecting a subject into a clinical trial may comprise (a) providing a biological sample obtained from a subject and measuring, in the sample, microvillus length; and (b) selecting the subject into a clinical trial when the subject is determined to be likely to respond to an inflammatory bowel disease therapy based on the microvillus length.

In addition to using a measurement of microvillus length in any of the above embodiments, one or more additional factors (e.g., gene expression and ileal intestinal epithelial cell (IEC) pyroptosis) can be calculated and may be used. Mathematical operations other than an average may also be used. For instance, various statistical models (e.g., linear regressions, LME curves, LOESS curves, etc.) in conjunction with other known biomarkers may be used.

The design of clinical trials for IBD therapies can be greatly aided by the methods disclosed herein. Many clinical trials are designed to test the efficacy of therapeutic agents that target a specific pathophysiological changes which can be influenced by disease severity among other factors. As discussed above in Section II, the efficacy of these various agents can be improved by administering the agents to subjects that are responsive or likely to be responsive to a therapeutic agent, as measured by methods disclosed herein and illustrated. Accordingly, measuring microvillus length as described herein prior to selecting a subject in a clinical trial, in particular into a treatment arm of a clinical trial, may result in smaller trials and/or improved outcomes.

In one example, the present disclosure provides a method for selecting a subject into a clinical trial, the method comprising (a) providing a biological sample obtained from a subject and measuring, in the sample, microvillus length; (b) comparing the microvillus length to a pre-determined value; (c) determining the subject as responsive to an inflammatory bowel disease therapy; and (d) selecting the subject into a clinical trial when the microvillus length is the same or above the pre-determined value, where the predetermined value is the microvillus length in a control population responsive to the inflammatory bowel disease therapy.

In still another example, a method for selecting a subject into a clinical trial, the method comprising (a) providing a biological sample obtained from a subject and measuring, in the sample, microvillus length; (b) comparing the microvillus length to a pre-determined value; (c) determining the subject as responsive to an inflammatory bowel disease therapy; and (d) selecting the subject into a clinical trial when the microvillus length is above the pre-determined value, where the predetermined value is the microvillus length in a control population non-responsive to the inflammatory bowel disease therapy.

In another example, a method for selecting a subject into a clinical trial, the method comprising (a) providing a biological sample obtained from a subject and measuring, in the sample microvillus length; (b) determining the subject as responsive to an inflammatory bowel disease therapy; and (c) selecting the subject into a clinical trial when the microvillus length is at least about 1.7 μm or above.

In another example, a method for selecting a subject into a clinical trial, the method comprising (a) providing a biological sample obtained from a subject and measuring, in the sample microvillus length; (b) determining the subject as responsive to an inflammatory bowel disease therapy; and (c) enrolling the subject into a clinical trial when the microvillus length is at least between about 1.35 μm and about 1.55 μm.

In each of the above embodiments, the methods may further comprise administering a pharmaceutical composition to the subject selected for the clinical trial.

General Techniques

The practice of the present disclosure will employ, unless otherwise indicated, conventional techniques of molecular biology (including recombinant techniques), microbiology, cell biology, biochemistry, and immunology, which are within the skill of the art. Such techniques are explained fully in the literature, such as Molecular Cloning: A Laboratory Manual, second edition (Sambrook, et al., 1989) Cold Spring Harbor Press; Oligonucleotide Synthesis (M. J. Gait, ed. 1984); Methods in Molecular Biology, Humana Press; Cell Biology: A Laboratory Notebook (J. E. Cellis, ed., 1989) Academic Press; Animal Cell Culture (R. I. Freshney, ed. 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds. 1993-8) J. Wiley and Sons; Methods in Enzymology (Academic Press, Inc.); Handbook of Experimental Immunology (D. M. Weir and C. C. Blackwell, eds.): Gene Transfer Vectors for Mammalian Cells (J. M. Miller and M. P. Calos, eds., 1987); Current Protocols in Molecular Biology (F. M. Ausubel, et al. eds. 1987); PCR: The Polymerase Chain Reaction, (Mullis, et al., eds. 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practice approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds. Harwood Academic Publishers, 1995); DNA Cloning: A practical Approach, Volumes I and II (D. N. Glover ed. 1985); Nucleic Acid Hybridization (B. D. Hames & S. J. Higgins eds. (1985»; Transcription and Translation (B. D. Hames & S. J. Higgins, eds. (1984»; Animal Cell Culture (R. I. Freshney, ed. (1986»; Immobilized Cells and Enzymes (IRL Press, (1986»; and B. Perbal, A practical Guide To Molecular Cloning (1984); F. M. Ausubel et al. (eds.).

When introducing elements of the present disclosure or the preferred aspects(s) thereof, the articles "a," "an," "the," and "said" are intended to mean that there are one or more of the elements. The terms "comprising," "including," and "having" are intended to be inclusive and mean that there may be additional elements other than the listed elements.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

As various changes could be made in the above-described materials and methods without departing from the scope of the invention, it is intended that all matter contained in the above description and in the examples given below, shall be interpreted as illustrative and not in a limiting sense.

EXAMPLES

The following examples are included to demonstrate various embodiments of the present disclosure. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1: Epithelial Cell Biomarkers are Predictive of Response to Biologic Agents in Crohn's Disease Biologics are antibodies targeting specific inflammatory pathways that have been used for the treatment of moderate-to-severe inflammatory bowel disease (IBD), including Crohn's disease (CD) and ulcerative colitis (UC), for over two decades. There are several classes in clinical use, including anti-tumor necrosis factor (TNF), anti-integrin, and anti-interleukin 12/23 (IL-12/23) antibodies. IBD is a heterogeneous group of diseases with highly variable disease phenotypes and clinical courses, and patients will likely have different responses to each biologic class depending on their specific disease subtype. Despite widespread clinical adoption of anti-TNF therapy, nearly half of the CD patients placed on biologics do not experience clinical response, resulting in dramatic increase in healthcare costs without significant improvement in outcomes. The annual costs of IBD treatment have increased by 30% within the last 5 years, and IBD-related hospitalizations quadrupled from 1998 to 2015.

Over the past decade, advances in disease pathogenesis from genomics, proteomics, and microbial and host metabolomic studies, also known as "multi-omics" approaches have identified key factors responsible for ongoing mucosal inflammation in IBD. The majority of effort to date has focused on the discovery and validation of biomarkers that can predict response to anti-TNF therapy. Mucosal and blood biomarkers that can predict responses to anti-TNFs using the multi-omics approach include oncostatin M, TNFR2 and IL13RA2, and TREM1. However, integrating them into routine clinical care has not yet occurred.

Recent work has discovered microvillus gene expression to play a role in the pathogenesis of mucosal inflammation and is altered in CD patients. Moreover, ileal microvillus length (MVL), was found to be a good cellular readout of the gene expression data, and ileal microvillus length was shown to be reduced in patients with active CD but increased with ustekimumab therapy. However, its predictive value for response to biologic therapies is unknown.

It was also recently demonstrated that a novel mucosal biomarker, ileal intestinal epithelial cell (IEC) pyroptosis, an inflammatory form of cell death in the intestine, was predictive of clinical response to vedolizumab therapy in CD patients. In that multicenter retrospective cohort study, 89% of vedolizumab-treated patients with an ileal IEC pyroptosis level<14 positive cells per 1,000 IECs achieved clinical response.

Given the above, the current study aimed to ascertain the predictive value of ileal microvillus length for therapeutic response to two biologics agents, ustekinumab and vedolizumab, in CD patients. Additionally, the correlation between the 2 epithelial cell biomarkers, ileal microvillus length and ileal IEC pyroptosis, in vedolizumab-treated CD patients was calculated. Finally, the utility of combining these biomarkers in order to discriminate responders from non-responders to vedolizumab in patients with CD was evaluated.

Methods

Study design and population. This study utilized 2 different cohorts, both prospective and retrospective, to address the various aims. To assess the predictive value of ileal microvillus length for response to ustekinumab in CD, a prospective cohort was used. This cohort consisted of patients enrolled from American study sites of the pivotal UNITI-2 randomized controlled trial of ustekinumab for CD. For the purpose of this study, patients with active ileal or ileocolonic disease who had ileal biopsies obtained were included.

For all other aims which involved vedolizumab-treated CD patients, specifically investigating the association between ileal microvillus length and response to vedolizumab, correlating ileal microvillus length and ileal IEC pyroptosis, and determining the utility of combining these biomarkers to differentiate responders from non-responders to vedolizumab, a multicenter retrospective cohort was used. This cohort consisted of CD patients from 5 IBD centers across the United States (Cleveland Clinic Foundation, Houston Methodist Hospital, University of Florida, University of Pennsylvania, and Washington University). Patients aged 18-80 years with a confirmed diagnosis of CD based on standard clinical, radiological, endoscopic, and histological criteria who had been prescribed vedolizumab for moderate-to-severe CD, disease flare, corticosteroid dependence, failure of other biologic therapies, or allergies or adverse reactions to other agents, were included. Patients were required to have undergone colonoscopy with ileal biopsies prior to the initiation of vedolizumab. Individual patient charts were reviewed in the electronic medical records to obtain all clinical information. The study protocol was reviewed and approved by the Institutional Review Board at each study site.

Outcomes. For the aim of evaluating the predictive value of ileal microvillus length for response to ustekinumab using the prospective randomized cohort, the following outcomes were assessed at 8 weeks post-induction: clinical response, defined as a reduction of Crohn's Disease Activity Index (CDAI) of>100 points from pre-treatment baseline; clinical remission, defined as CDAI<150; and endoscopic response, defined as a ≥50% reduction from baseline Simple Endoscopic Score for Crohn's Disease (SES-CD) score. The primary outcome was clinical response to ustekinumab stratified by pre-treatment ileal microvillus length, using a threshold of 1.7 μm, which corresponds to 75% of the mean ileal microvillus length of the healthy general population. Pre-specified secondary outcomes included correlations between pre-treatment ileal microvillus length and baseline clinical activity, as measured by the CDAI, and baseline endoscopic activity, as measured by the SES-CD.

For all other aims involving vedolizumab-treated CD patients from the multicenter retrospective cohort, the following outcomes were evaluated approximately 6 months after initiation of therapy: clinical response, defined as a reduction of Harvey-Bradshaw Index (HBI) of>5 points from pre-treatment baseline; and clinical remission, defined as HBI<5. The primary outcome was clinical response to vedolizumab by pre-treatment ileal microvillus length. The correlations between pre-treatment ileal microvillus length and baseline HBI and baseline SES-CD were also calculated.

Assessment of ileal microvillus length. One set of tissue samples were prepared for H&E-stained tissue sections. Brightfield microscopy of H&E-stained ileal resection margins or biopsy tissue specimens were acquired with an Olympus BX51 microscope equipped with UPlanFL 10×/0.30, 20×/0.50, 40×/0.75, and 100×/1.30 Oil Iris objective lenses, an Olympus DP70 camera and DP Controller software or an Olympus DP22 camera and CellSens Standard v1.17 software. The stained tissue was viewed and measurements were made with a live video feed in CellSens Standard software. In another scenario, the stained tissue was imaged and measurements were made using ImageJ software. To quantify microvillus length and cell height, 5 enterocytes were measured per villus on 10 villi per sample, for a total of 50 cells measured per sample. Measured cells were visualized with the 100× objective lens and were located in the top one-third of a villus, where enterocytes have a matured brush border, in regions with well-oriented epithelial cells. It was previously demonstrated high inter-observer agreement with this method.

Assessment of ileal IEC pyroptosis. Ileal biopsies collected from study patients during colonoscopy before the initiation of vedolizumab therapy were sectioned and stained for activated caspase stains using Maximus Biological Assay staining kits (Maximus Diagnostics LLC, Little Rock, AR) and anti-CD3 antibody to differentiate intraepithelial lymphocytes from IECs. Samples with at least 10 intact crypts/villi were analyzed for each patient to quantitate IEC pyroptosis by two blinded gastrointestinal pathologists (EUY and FDA). IECs were manually counted in 10 villi for the derivation of pyroptosis normalized per 1,000 IECs. Confocal images of the slides were acquired with Zeiss LSM 880 confocal microscope equipped with Airyscan (Zeiss USA, Dublin, CA).

Sample size calculation. The sample size calculation was based on the assumption that there would be a difference in clinical response rate to ustekinumab of at least 30% between patients on therapy vs. placebo by ileal microvillus length cutoff value. A total of 84 patients (42 per group) would be needed to achieve 80% statistical power with a type I error (α) of 0.05, assuming equal numbers of patients in each group. Similarly, for vedolizumab response, we assumed that an ileal microvillus length cutoff or range could be identified that would provide a 30% difference in clinical response rate between patients at either ends of this cutoff or range. A total of 84 patients (42 per group) would be needed to achieve 80% statistical power with a type I error (a) of 0.05, assuming equal numbers of patients in each group.

Statistical analysis. Baseline demographic, disease-related, and medication variables were collected and included, respectively: age, sex, race/ethnicity, and body mass index; disease phenotype, location, and activity (both clinical and endoscopic); and concomitant use of immunomodulators and corticosteroids, as well as history of prior anti-TNF exposure. Continuous variables were described using means with standard deviations or medians with interquartile ranges; categorical variables were expressed as numbers and proportions.

The probabilities of clinical response to ustekinumab and vedolizumab by pre-treatment ileal microvillus length were plotted graphically. Clinical and endoscopic outcomes stratified by ileal microvillus length thresholds or ranges were compared using Fisher exact tests. Likelihood ratio tests were used to assess for effect modification by ileal microvillus length. Spearman correlation coefficients were calculated to determine the relationships between ileal microvillus length or ileal IEC pyroptosis and baseline clinical and endoscopic activity. For prediction of clinical response to vedolizumab, an ileal IEC pyroptosis threshold of 14 positive cells/1,000 IECs was used. The value of ileal microvillus length alone or in combination with ileal IEC pyroptosis for prediction of clinical response to vedolizumab was compared using Fisher's exact test. All analyses were performed using STATA statistical software (StataCorp LP, College Station, Texas). Two-sided p-values<0.05 were considered statistically significant.

Results (i) Response to Ustekinumab in the Randomized Prospective Cohort

For determination of ustekinumab response, a total of 106 CD patients from UNITI-2 (placebo=36, ustekinumab=70) biopsies were stained and analyzed, of which 95 patients (90%) had sufficient samples for analysis of ileal microvillus length. Baseline patient characteristics between placebo- and ustekinumab-treated patients were comparable (Table 1). The rate of clinical response was significantly higher in the ustekinumab-treated group: 65% (40/62) vs. 39% (13/33) (p=0.03), with a similar trend in clinical remission rate of 42% (26/62) vs. 24% (8/33, p=0.12).

Figure 1B:
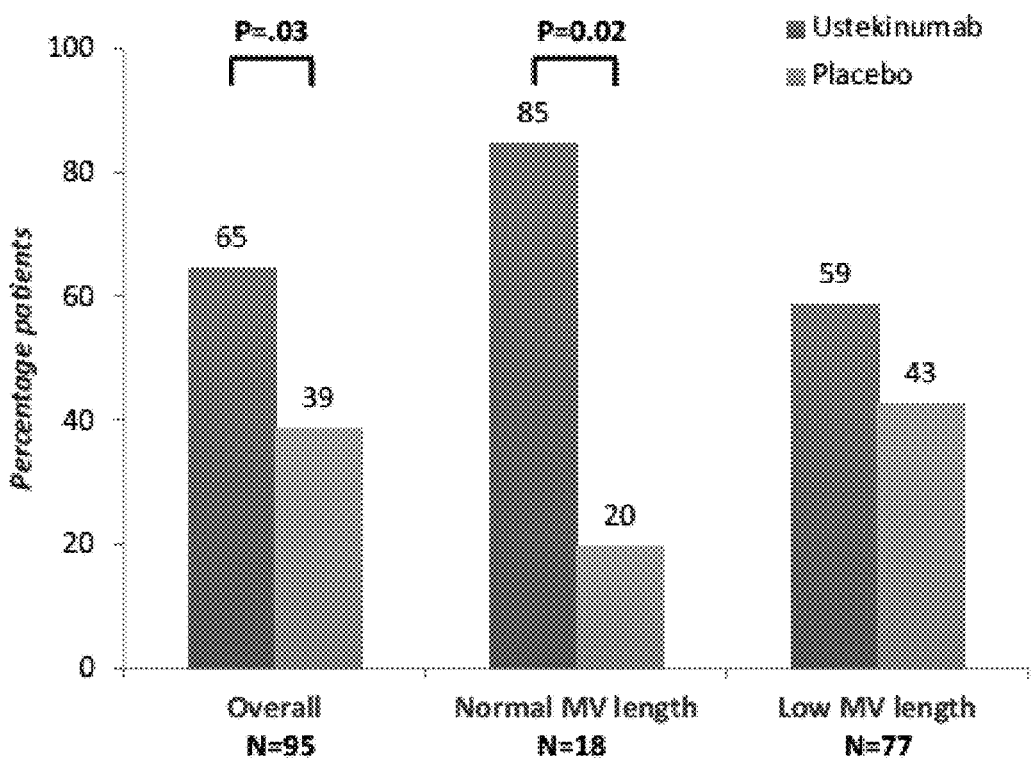
Figure 1C:
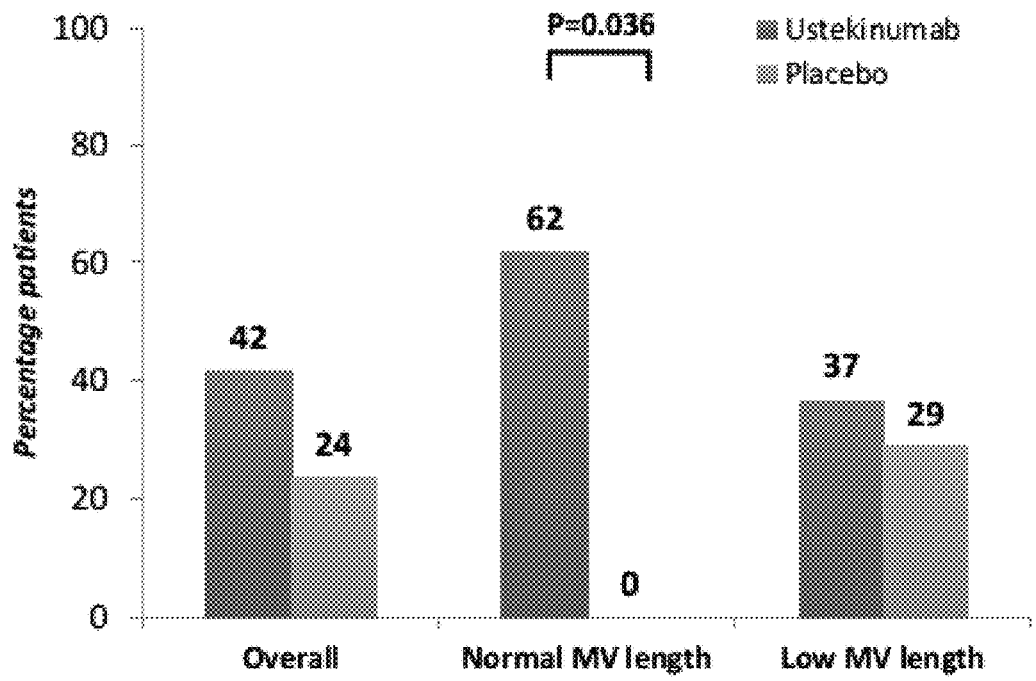
Figure 1D:
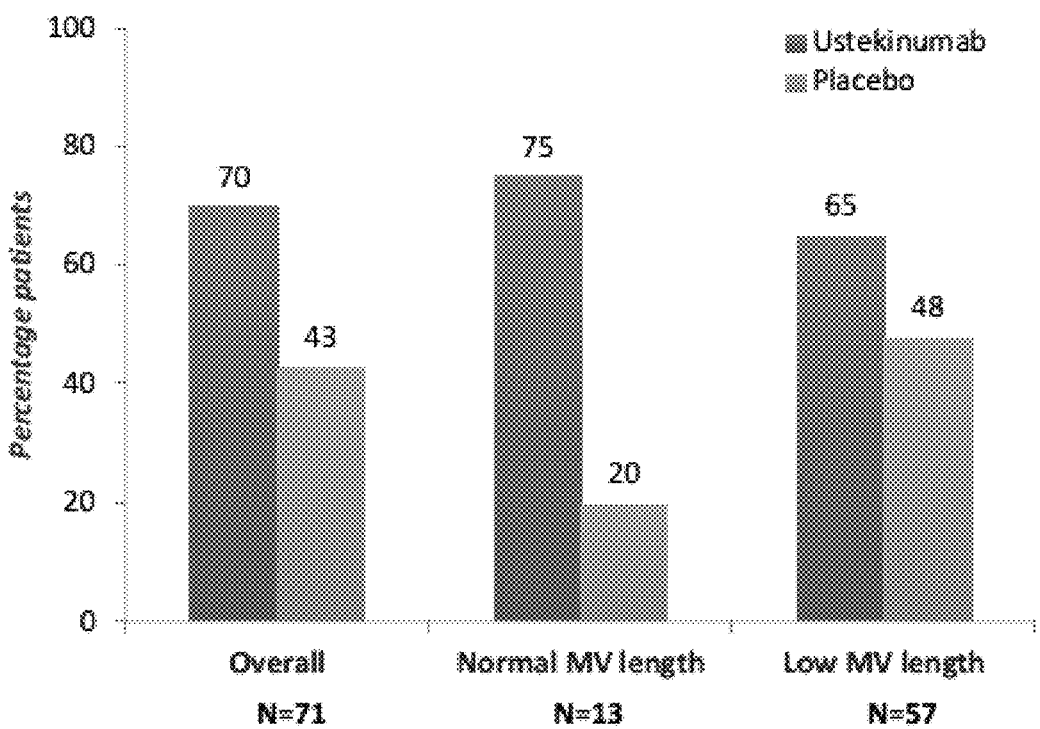

As a continuous variable, ileal microvillus length was found to be an effect modifier of response to ustekinumab (p=0.043), with the probability of response to ustekinumab having a positive linear relationship to ileal microvillus length with higher response rates as microvillus length increased, while placebo response had a negative linear relationship to ileal microvillus length with lower response rates as increased microvillus length (FIG. 1A). Using the 75th percentile of ileal microvillus length in the healthy general population of 1.7 μm as a threshold, the greatest therapeutic effect and differences were seen in the normal microvillus length group (>1.7 μm): clinical response rate of 85% (11/13) with ustekinumab vs. 20% (1/5) with placebo (Δ vs. placebo=65%, p=0.02) (FIG. 1B); clinical remission rate of 62% (8/13) with ustekinumab vs. 0% (0/5) with placebo (Δ vs. placebo=60%, p=0.036) (FIG. 1C). In the low microvillus length group (<1.7 μm), rates were 59% (28/49) with ustekinumab vs. 46% (12/28) with placebo (Δ vs. placebo=13%, p=0.17) for clinical response (FIG. 1B), and 37% (18/49) vs. 29% (8/28, Δ vs. placebo=8%, p=0.62) for clinical remission (FIG. 1C). The therapeutic effect by endoscopic response, available in 71 patients, was also greater in patients with normal ileal microvillus length: 75% (6/8) vs. 20% (1/5), Δ vs. placebo=55% (p=0.053); compared to low microvillus length patients, with rates of 65% (24/35) vs. 48% (11/23), Δ vs. placebo=17% (p=0.11) (FIG. 1D).

Figure 2A:
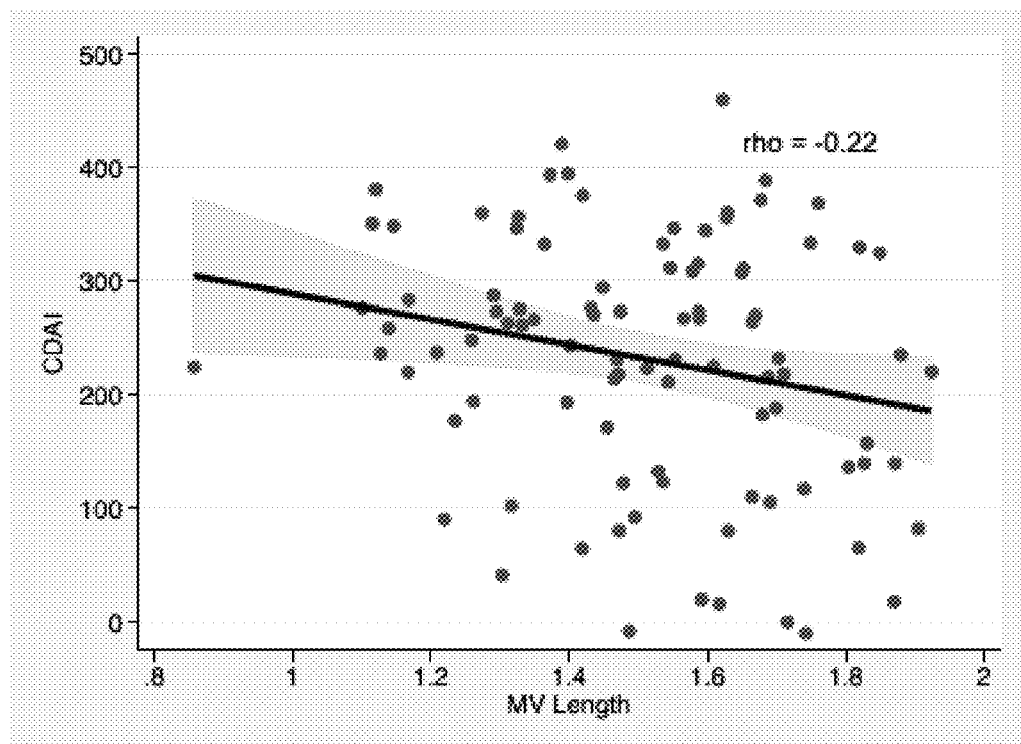
FIG. 2A and FIG. 2B show the correlation between ileal microvillus length and baseline disease activity indices.
Figure 2B:
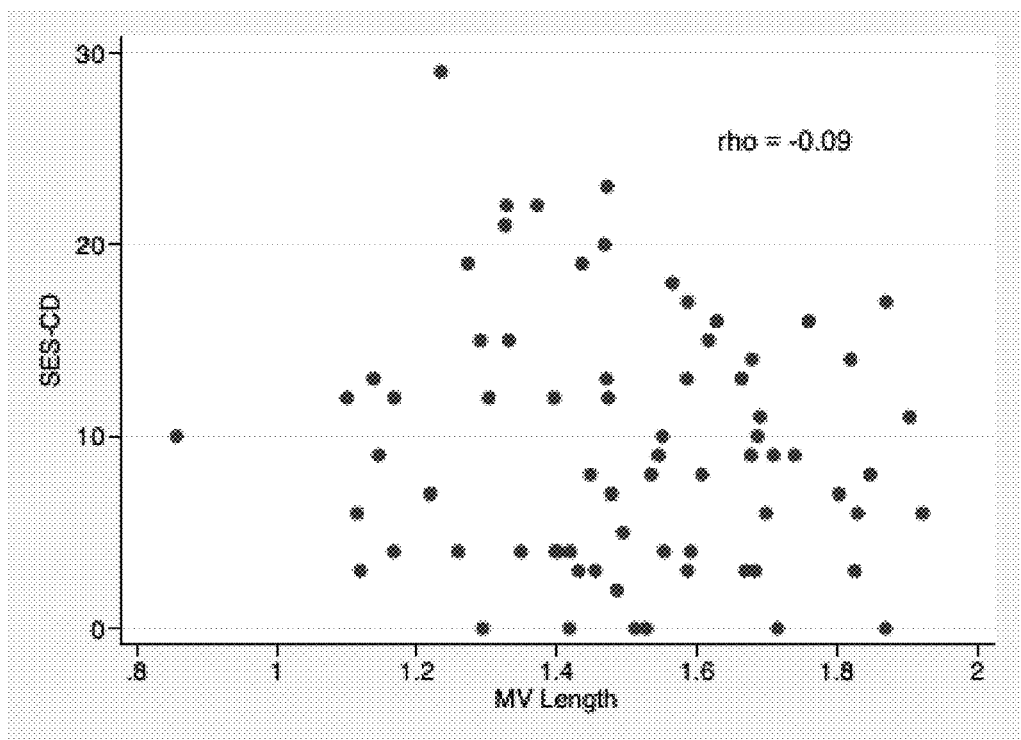

With respect to relationship with baseline disease activity, pre-treatment ileal microvillus length was not correlated with baseline clinical disease activity, as measured by CDAI (rho=−0.22) (FIG. 2A). Ileal microvillus length was not correlated with baseline endoscopic disease activity by SES-CD (rho=−0.09) (FIG. 2B).

TABLE 1

Baseline characteristics of the ustekinumab response cohort from UNITI-2

|  | Placebo (N = 36) | Ustekinumab (N = 70) | p-value |
|---|---|---|---|
| Mean age, years ± SD | 43 ± 14 | 38 ± 12 | 0.10 |
| Female sex, N (%) | 18 (50) | 40 (57) | 0.48 |
| Caucasian | 32 (89) | 14.4 (8.6) |  |
| African American | 1 (3) | 6 (9) |  |
| Asian or other | 3 (9) | 4 (5) |  |
| Average BMI ± SD, kg/m$^2$ | 26.2 ± 6.0 | 26.0 ± 5.8 | 0.46 |
| Disease duration, y [IQR] | 6.4 [2.4, 15.9] | 4.0 [1.5, 13.4] | 0.15 |
| Disease phenotype, N (%) |  |  |  |
| Fistulizing | 2 (6) | 5 (7) | 0.76 |
| Fibrostenotic | 8 (22) | 14 (20) | 0.18 |
| Disease location, N (%) |  |  | 0.42 |
| Ileum only | 12 (33%) | 17 (24%) |  |
| Colon only | 19 (53%) | 34 (49%) |  |
| Ileum and colon | 5 (14%) | 18 (26%) |  |
| Prior anti-TNF exposure, N(%) | 14 (48%) | 27 (40%) | 0.43 |
| CRP | 2.8 [1.0, 14.4] | 5.1 [2.4, 10.6] | 0.55 |
| Fecal calprotectin, median ug/g [IQR] | 281.9 [76.0, 1252.9] | 221.5 [28.0, 560.8] | 0.31 |

(ii) Response to Vedolizumab in the Multicenter Retrospective Cohort

Figure 3A:
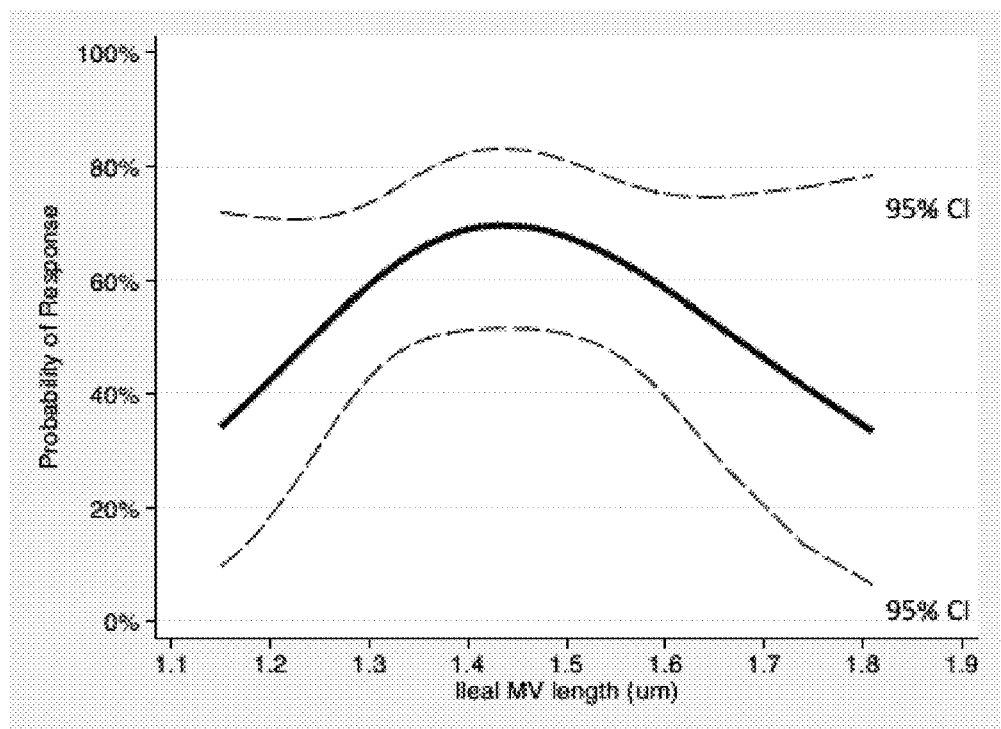
FIG. 3A, FIG. 3B, and FIG. 3C show ileal microvillus length is predictive of response to vedolizumab in CD patients from the multicenter retrospective cohort.
Figure 3B:
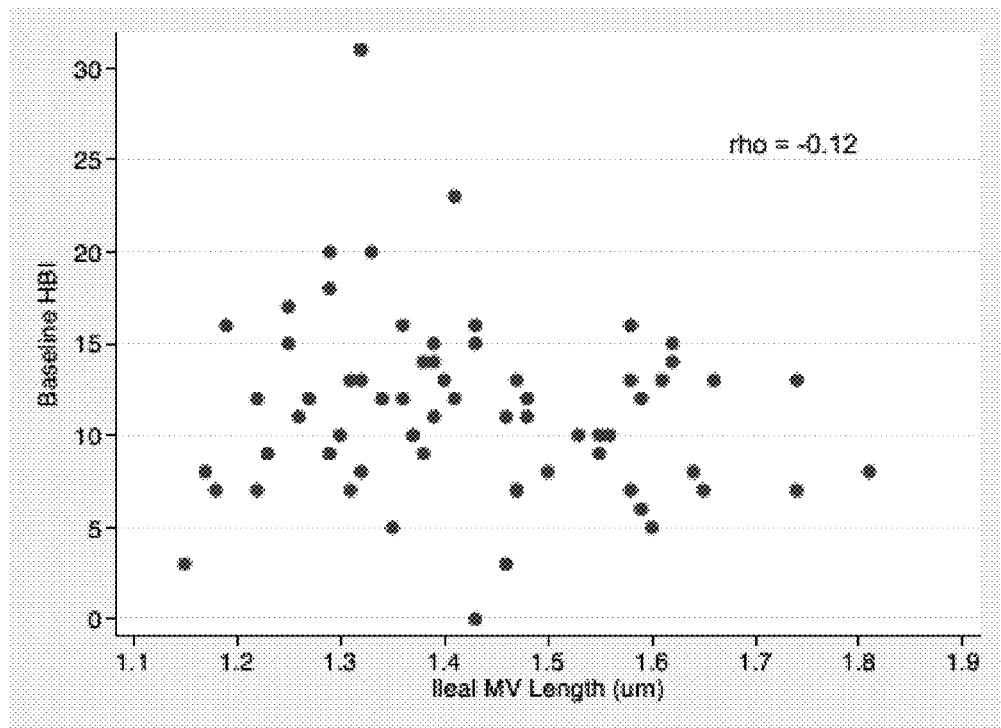
Figure 3C:
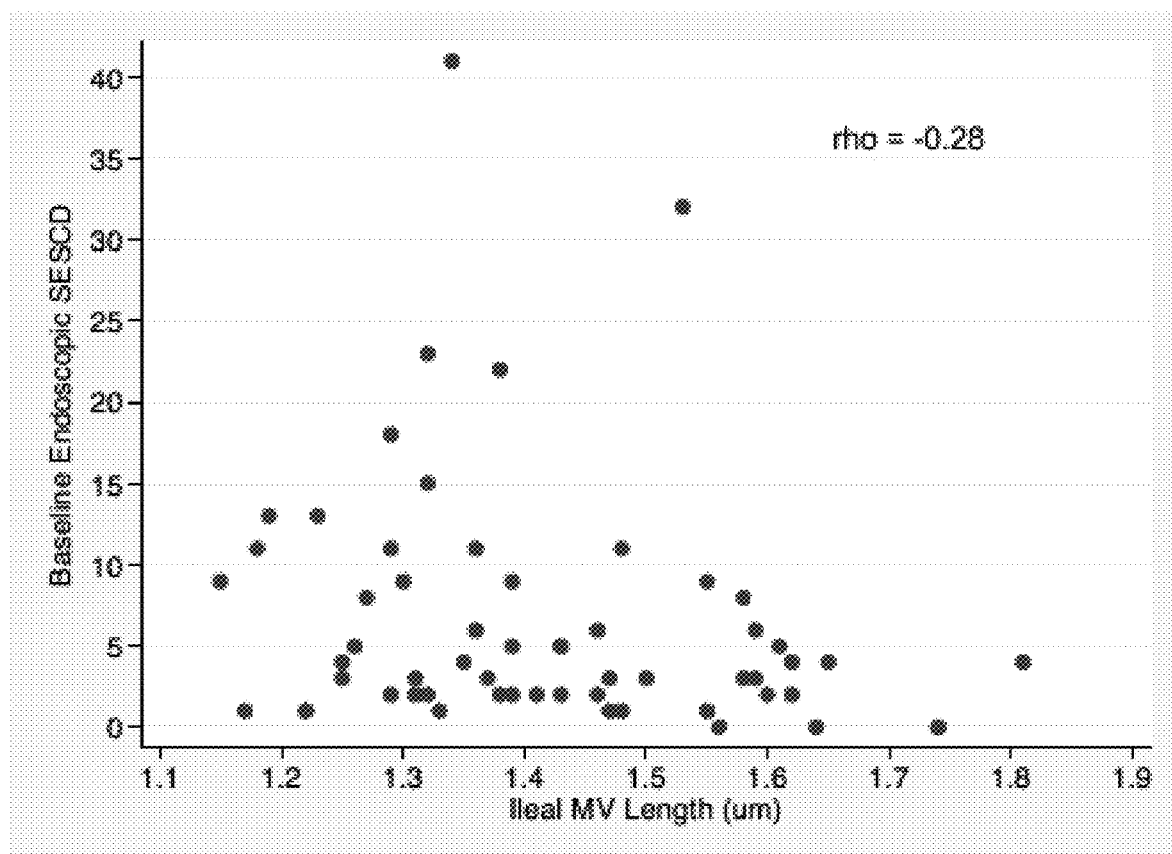

For prediction of response to vedolizumab, 86 CD patients from the 5 IBD centers had ileal biopsies stained and analyzed, of which 64 had adequate samples for analysis of both ileal microvillus length and ileal IEC pyroptosis. The overall clinical response rate to vedolizumab was 59% (38/64). There were no significant differences in baseline patient characteristics, disease characteristics, concomitant medication use, or prior anti-TNF exposures histories between responders (N=38) and non-responders (N=26) (Table 2). The probability curve of clinical response to ileal microvillus length was bell-shaped, with a range of 1.35-1.55 μm associated with a significantly higher response rate of 82% (14/17), compared to 51% (24/47) for values outside this range (p=0.04, FIG. 3A). Pre-treatment ileal microvillus length did not correlate with either baseline clinical disease activity by HBI (rho=−0.12) (FIG. 3B), or baseline endoscopic disease activity by SES-CD (rho=−0.28) (FIG. 30).

Figure 4A:
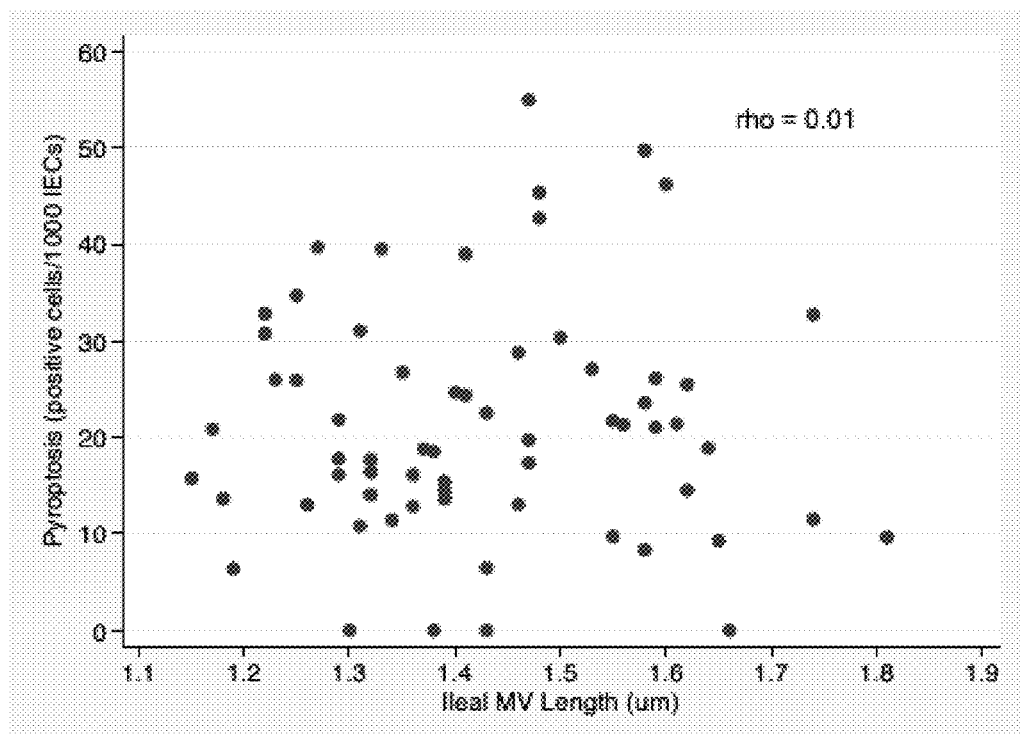
FIG. 4A and FIG. 4B show ileal microvillus length and ileal IEC pyroptosis are independent and synergistic biomarkers for prediction of response to vedolizumab in CD.
Figure 4B:
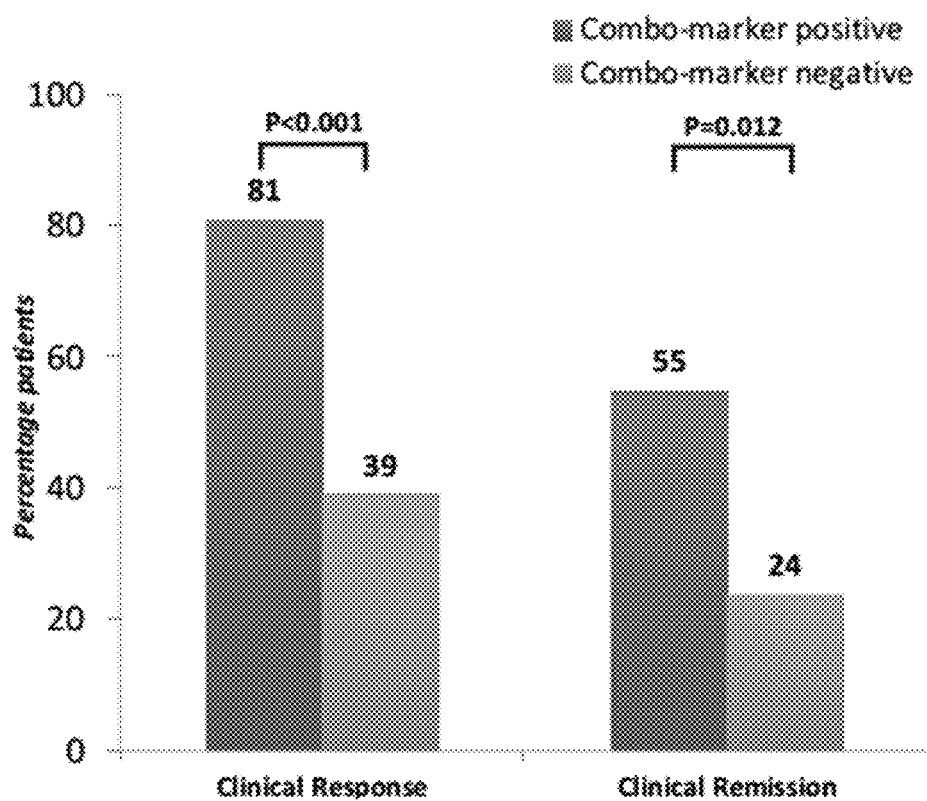

Pre-treatment ileal microvillus length also did not correlate with pre-treatment ileal IEC pyroptosis (rho=0.01) (FIG. 4A). Moreover, the combination criteria of ileal IEC. pyroptosis level<14 positive cells/1,000 IECs and ileal microvillus length of 1.35-1.55 μm was associated with a vedolizumab clinical response rate of 81% (25/31), compared to 39% (13/33) for those with neither criterion (p<0.001); corresponding rates of clinical remission rates were 55% (17/31) vs. 24% (8/33) in the 2 groups (p=0.012), respectively (FIG. 4B). The combination criteria could identify 66% of responders (25/38), compared to 42% of responders using ileal IEC pyroptosis alone and 37% of responders using microvillus length alone. Additionally, fulfillment of neither criterion identified the majority (77%, 20/26) of non-responders to vedolizumab.

TABLE 2

Baseline Characteristics of Vedolizumab Response Cohort

| | Responders (N = 38) | Non-Responders (N = 26) | p-value | Total (N = 64) |
|---|---|---|---|---|
| Mean age, years ± SD | 46 ± 15 | 42 ± 13 | 0.23 | 44 ± 14 |
| Female sex, N (%) | 18 (47) | 13 (50) | 0.84 | 33 (52) |
| Race/Ethnicity, N (%) | | | | |
| Caucasian | 32 (84) | 19 (73) | | 51 (80) |
| Hispanic | 2 (5) | 0 (0) | | 2 (3) |
| African American | 0 (0) | 3 (12) | | 3 (5) |
| Asian | 0 (0) | 2 (8) | | 2 (3) |
| Other | 4 (11) | 2 (8) | | 6 (9) |
| Average BMI ± SD, kg/m$^2$ | 26.9 ± 7.5 | 25.8 ± 5.4 | 0.49 | 26.5 ± 6.7 |
| Disease phenotype, N (%) | | | | |
| Fistulizing | 9 (24) | 8 (31) | 0.53 | 17 (27) |
| Fibrostenotic | 7 (18) | 7 (27) | 0.42 | 14 (22) |
| Disease Location, N (%) | | | 0.41 | |
| Ileum only | 12 (32) | 5 (19) | | 17 (27) |
| Colon only | 5 (13) | 6 (23) | | 11 (17) |
| Ileum and colon | 21 (55) | 15 (58) | | 36 (56) |
| Concomitant Medication Use, N (%) | | | | |
| Immunomodulator | 28 (74) | 20 (77) | 0.77 | 48 (75) |
| Corticosteroids | 28 (74) | 18 (69) | 0.70 | 46 (72) |
| Prior anti-TNF exposure | 32 (84) | 24 (92) | 0.34 | 56 (88) |

Discussion

At the present time, selection of biologic therapy in IBD is largely arbitrary. The transformational goal of future IBD therapy is the personalized selection of agents based on each individual patient's pathobiology. In this study using both prospective randomized and multicenter retrospective cohorts of CD patients, ileal microvillus length, an epithelial biomarker, was found to be predictive of response to two different biologic agents, ustekinumab and vedolizumab. Additionally, combining this mucosal biomarker with another recently discovered biomarker, ileal IEC pyroptosis, was associated with high rates of clinical response to vedolizumab in CD and also identified the majority of non-responders to vedolizumab. These findings suggest that epithelial cellular function may play an important role not only in the pathogenesis of IBD but also in guiding the selection of biologic agents for individual CD patients.

Interestingly, the probability curves for clinical response by ileal microvillus length for the 2 biologic drugs evaluated were different: a linear relationship for ustekinumab and a bell-shaped curve for vedolizumab. As was observed with ileal IEC pyroptosis in vedolizumab-treated CD patients, pre-treatment ileal microvillus length did not correlate with either baseline clinical or endoscopic disease activity in both ustekinumab-treated and vedolizumab-treated CD patients. Additionally, these 2 mucosal biomarkers at pre-treatment did not correlate with each other and seem largely independent in terms of utility to predict response to vedolizumab in CD patients with effects that were nearly additive.

There is an urgent and unmet need in the care of patients with moderate-to-severe CD to personalize biologic therapy. The existing CD phenotypic classification system which focuses on inflammation and complications is not sufficient to guide treatment decisions for biologics, which are designed to target specific inflammatory pathways. Due to limited therapeutic efficacy and lack of personalized treatment, IBD-related healthcare outcomes and costs have not improved with the widespread clinical adoption of biologic therapies over the past 2 decades. The annual costs of IBD treatment have increased by 30% within the last 5 years, and IBD-related hospitalizations quadrupled from 1998 to 2015. Nearly half of CD patients placed on a given biologic therapy do not have a clinical response, likely because the therapy chosen is not targeting the specific inflammatory pathway(s) driving the disease.

To address this need, some recent effort has focused on the discovery of biomarkers that can predict therapeutic responses to various biologics. Several mucosal biomarkers have been reported to be associated with response to anti-TNF agents in CD: oncostatin M, TNFR2 and IL13RA2, and TREM1. For example, high pre-treatment levels of transmembrane TNF positive cells were observed to be positively associated with response to adalimumab, whereas high pre-treatment levels of oncostatin M were found to be negatively associated with response to infliximab and goliumumab. With respect to predicting response to anti-integrin therapy, high mucosal gene expressions of αE and granzyme A were demonstrated to be associated with improved response to etrolizumab in patients with UC.

Over the past decade, advances in disease pathogenesis from multi-omics approaches have identified that epithelial barrier function is responsible for ongoing mucosal inflammation in IBD. Advances in innate immunology have identified ileal IEC pyroptosis as a possible contributor to mucosal barrier dysfunction and inflammation in IBD. Lower levels of ileal IEC pyroptosis were associated with increased clinical response and remission to vedolizumab in patients with CD. Based on these emerging data, another mucosal biomarker that may play a key role in epithelial cell biology and function, ileal microvillus length, as was recognized to be a measure of cellular absorption and metabolism. The results of the present example extend the use of microvillus length to enhance the ability to predict response to vedolizumab in CD, with additive and synergistic effects of the combination of the two independent biomarkers. Additionally, this example was able to extend biomarker-assisted prediction of clinical and endoscopic outcomes to ustekinumab-treated patients.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

The term "about" or "approximately" means within an acceptable error range for the particular value as determined by one of ordinary skill in the art, which will depend in part on how the value is measured or determined, i.e., the limitations of the measurement system. For example, "about" can mean within an acceptable standard deviation, per the practice in the art. Alternatively, "about" can mean a range of up to ±20%, preferably up to ±10%, more preferably up to ±5%, and more preferably still up to ±1% of a given value. Alternatively, particularly with respect to biological systems or processes, the term can mean within an order of magnitude, preferably within 2-fold, of a value. Where particular values are described in the application and claims, unless otherwise stated, the term "about" is implicit and in this context means within an acceptable error range for the particular value.

It should also be understood that, unless clearly indicated to the contrary, in any methods claimed herein that include more than one step or act, the order of the steps or acts of the method is not necessarily limited to the order in which the steps or acts of the method are recited.

As used herein, the term "subject" refers to a mammal, preferably a human. The mammals include, but are not limited to, humans, primates, livestock, rodents, and pets. A subject may be waiting for medical care or treatment, may be under medical care or treatment, or may have received medical care or treatment.

As used herein, the term "healthy control group," "normal group" or a sample from a "healthy" subject means a subject, or group subjects, who is/are diagnosed by a physician as not suffering from inflammatory bowel disease, or a clinical disease associated with IBD based on qualitative or quantitative test results. A "normal" subject is usually about the same age as the individual to be evaluated, including, but not limited, subjects of the same age and subjects within a range of 5 to 10 years.

What is claimed is:

1. A method for treating inflammatory bowel disease (IBD) in a human subject having IBD, comprising:
    (a) obtaining results of measuring microvillus length in a human ileal tissue sample obtained from a human subject having IBD that show a length greater than 1.7 µm; and
    (b) treating said subject with anti-IL12/23 therapy.

2. The method of claim 1, wherein the anti-IL-12/23 therapy is Ustekinumab.

3. The method of claim 1, wherein said IBD is Chron's Disease.

4. The method of claim 1, wherein said IBD is Ulcerative Colitis.

* * * * *